United States Patent [19]

Warshawsky et al.

[11] Patent Number: 5,491,141
[45] Date of Patent: Feb. 13, 1996

[54] 2-SUBSTITUTED INDANE-2-MERCAPTOACETYLAMIDE TRICYCLIC DERIVATIVES USEFUL AS INHIBITORS OF ENKEPHALINASE

[75] Inventors: Alan M. Warshawsky; Gary A. Flynn, both of Cincinnati, Ohio

[73] Assignee: Merrell Dow Pharmaceuticals Inc., Cincinnati, Ohio

[21] Appl. No.: 396,833

[22] Filed: Mar. 1, 1995

Related U.S. Application Data

[60] Division of Ser. No. 78,787, Jun. 17, 1993, Pat. No. 5,420,271, which is a continuation-in-part of Ser. No. 934,833, Aug. 24, 1992, abandoned.

[51] Int. Cl.$^6$ .......................... A61K 31/55; C07D 495/06
[52] U.S. Cl. .......................... 514/214; 540/520; 540/521
[58] Field of Search .............................................. 514/214

[56] References Cited

U.S. PATENT DOCUMENTS 5,420,271  5/1995  Warshawsky et al. ................. 540/521

*Primary Examiner*—Robert T. Bond
*Attorney, Agent, or Firm*—Charlotte L. Barney

[57] ABSTRACT

The present invention relates to novel 2-substitited indane-2-mercaptoacetylamide tricyclic derivatives which are useful as inhibitors of Enkephalise.

5 Claims, No Drawings

2-SUBSTITUTED INDANE-2-MERCAPTOACETYLAMIDE TRICYCLIC DERIVATIVES USEFUL AS INHIBITORS OF ENKEPHALINASE

CROSS-REFERENCE TO RELATED APPLICATION

This is division, of application Ser. No. 08/078,787, filed Jun. 17, 1993, now U.S. Pat. No. 5,420,271, which is a CIP of application Ser. No. 07/934,833, filed Aug. 24, 1992 now abandoned—which is herein incorporated by reference.

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins is inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration.

ANP refers to a family of naturally-occurring peptides which are involved in the homeostatic regulation of blood pressure, as well as sodium and water levels. ANPs have been found to vary in length from about 21 to about 126 amino acids with a common structural feature being one or more disulfide-looped sequences of 17 amino acids with various amino- and carboxy-terminal sequences attached to the cystine moiety. ANPs have been found to bind to specific binding sites in various tissues including kidney, adrenal, aorta, and vascular smooth muscle with affinities ranging from about 50 pico-molar (pM) to about 500 nano-molar (nM) [Needleman, *Hypertension* 7, 469 (1985)]. In addition, it is believed that ANP binds to specific receptors in the brain and possibly serves as a neuromodulator as well as a conventional peripheral hormone.

The biological properties of ANP involve potent diuretic/natriuretic and vasodilatory/hypotensive effects as well as an inhibitory effect on renin and aldosterone secretion [deBold, *Science* 230, 767 (1985)]. By inhibiting enkephalinase, the metabolic degradation of the naturally-occurring ANP is inhibited, thereby providing a potent ANP-mediated diuretic, natriuretic, hypotensive, hypoaldosteronemic effect. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

SUMMARY OF THE INVENTION

The present invention provides novel compounds of the Formula (I)

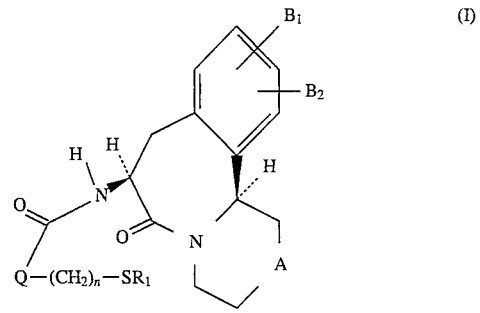

wherein $B_1$ and $B_2$ are each independently hydrogen; hydroxy; —$OR_2$ wherein $R_2$ is a $C_1$–$C_4$ alkyl or an Ar—Y group wherein Ar is aryl and Y is a hydrogen or $C_1$–$C_4$ alkyl; or, where $B_1$ and $B_2$ are attached to adjacent carbon atoms, $B_1$ and $B_2$ can be taken together with said adjacent carbons to form a benzene ring or methylenedioxy;

A is a bond, methylene, oxygen, sulfur, $NR_4$ or $NCOR_5$ wherein $R_4$ is hydrogen, a $C_1$–$C_4$ alkyl or an Ar—Y— group and $R_5$ is —$CF_3$ or a $C_1$–$C_{10}$ alkyl or an Ar—Y— group;

$R_1$ is hydrogen, acetyl, —$CH_2OC(O)C(CH_3)_3$ or benzoyl;

n is an integer 0 to 3; and

Q is a group of the formula

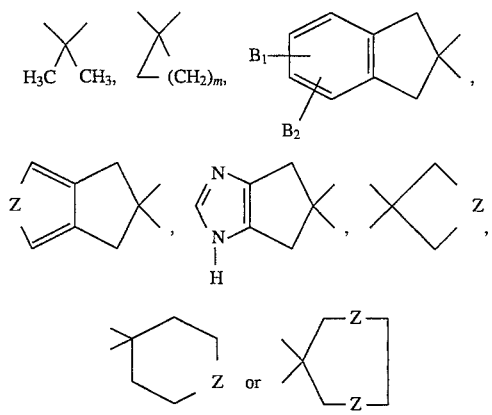

wherein Z is O, $NR_4$ or S; and m is an integer 1 to 5.

The present invention further provides a method of inhibiting enkephalinase in a patient in need thereof comprising administering to said patient an effective enkephalinase inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used herein, the term "$C_1$–$C_4$ alkyl" refers to a saturated straight or branched chain hydrocarbyl radical of one to four carbon atoms and includes methyl, ethyl, propyl, isopropyl, n-butyl, isobutyl, tertiary butyl and the like. The term "$C_1$–$C_{10}$ alkyl" refer to saturated straight or branched chain hydrocarbyl radicals of one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl, octyl, nonyl, or decyl and the like. The term "halogen", "halo", "halide" or "Hal" refers to a chlorine, bromine, or iodine atom. The term "BOC" refers to t-butyloxycarbonyl. The term "$C_1$–$C_4$ alkoxy" refers to a saturated straight or branched chain hydrocarboxy radical of one to four carbon atoms and includes methoxy, ethoxy, propoxy, isopropoxy, n-butoxy, isobutoxy, tertiary butoxy and the like.

As used herein, the term "Ar—Y—" refers to a radical wherein Ar is an aryl group and Y is a $C_0$–$C_4$ alkyl. The term "Ar" refers to a phenyl or naphthyl group unsubstituted or substituted with from one to three substituents selected from the group consisting of methylenedioxy, hydroxy, $C_1$–$C_4$ alkoxy, amino, nitro, fluoro and chloro. The term "$C_0$–$C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar—Y—" are phenyl, naphthyl, phenylmethyl or benzyl, phenylethyl, 3,4-methylenedioxyphenyl, m-aminophenyl, m-nitrophenyl, p-aminophenyl, p-nitrophenyl, p-methoxybenzyl, p-fluorobenzyl and p-chlorobenzyl.

Compounds of Formula (I) wherein Z is $NR_4$ and $R_4$ is hydrogen can form pharmaceutically acceptable salts with any non-toxic, organic or inorganic acid. Illustrative inorganic acids which form suitable salts include hydrochloric, hydrobromic, sulphuric and phosphoric acid and acid metals salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic, trifluoromethane sulfonic, 2-hydroxyethane sulfonic acid and p-toluenesulfonic acid.

The compounds of Formula (I) wherein A is —$CH_2$—, —O—, —S—, a bond or —$NR_4$— wherein $R_4$ is hydrogen can be prepared by utilizing procedures and techniques well known and appreciated by one of ordinary skill in the art. A general synthetic scheme for preparing these compounds is set for in Scheme A wherein all substituents are as previously defined unless otherwise defined.

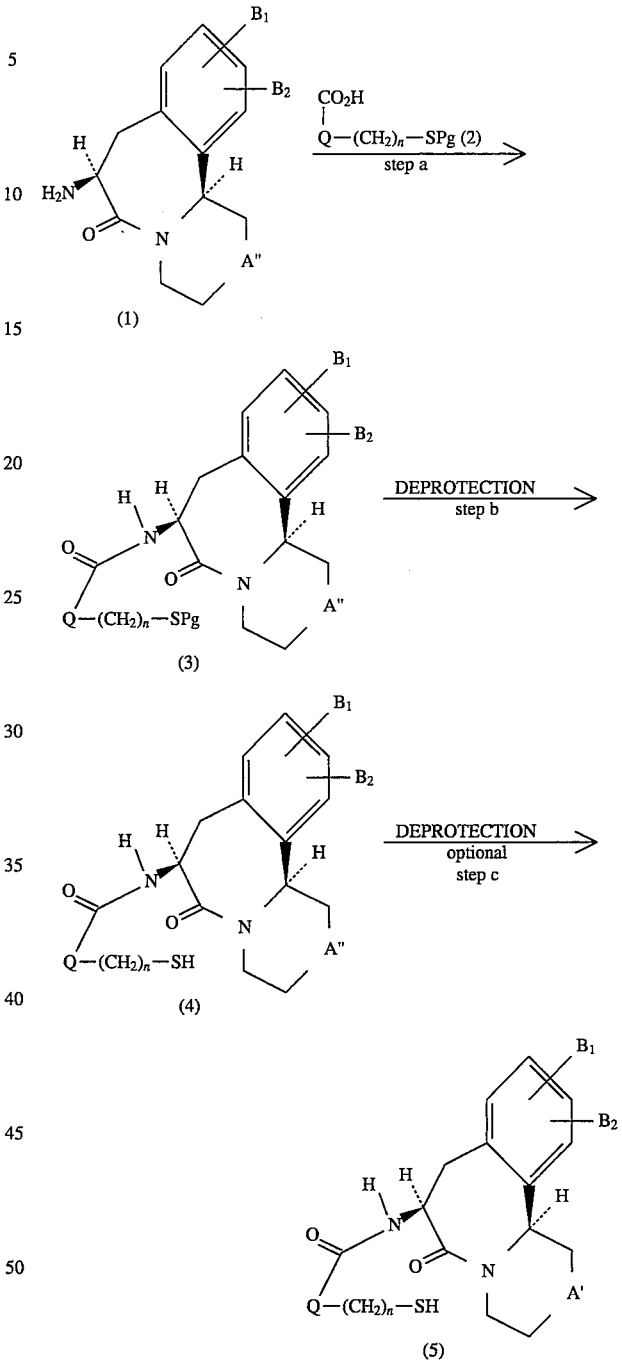

A" = —$CH_2$—, —O—, —S—, a bond or —N—Boc—
A' = —NH—

Scheme A provides a general synthetic procedure for preparing compounds of Formula (I) wherein Z is —$CH_2$—, —O—, —S—, a bond or —$NR_4$— wherein $R_4$ is hydrogen.

In step a, the appropriate amino tricyclic compound of structure (1) wherein Z is —$CH_2$—, —O—, —S—, a bond or —N-Boc is reacted with the appropriate protected thiol compound of structure (2) to give the corresponding thiol protected tricyclic compound of structure (3) wherein Z is —$CH_2$—, —O—, —S—, a bond or —N-Boc. For example, the appropriate amino tricyclic compound of structure (1) wherein Z is —$CH_2$—, —O—, —S—, a bond or —N-Boc can be reacted with the appropriate protected thiol compound of structure (2) in the presence of a coupling reagent such as EDC (1-ethoxycarbonyl-2-ethoxy-1,2-dihydroquinoline), DCC (1,3-dicyclohexylcarbodiimide), or diethylcyanophosponate in a suitable aprotic solvent, such as methylene chloride to give the appropriate thiol protected tricyclic compound of structure (3) wherein Z is —$CH_2$—, —O—, —S—, a bond or —N-Boc.

Alternatively, the protected thiol compound of structure (2) can be converted to the corresponding acid chloride, followed by reaction with the appropriate amino tricyclic compound of structure (1) wherein Z is —$CH_2$—, —O—, —S—, a bond or —N-Boc to give the appropriate thiol protected tricyclic compound of structure (3) wherein Z is —$CH_2$—, —O—, —S—, a bond or —N-Boc.

The selection and utilization of suitable thiol protecting groups, such as t-butyl and 4-methoxybenzyl, is well known to one of ordinary skill in the art and are described in "Protective Groups in Organic Syntheses", Theodora W. Greene, Wiley (1981).

In step b, the thiol protecting group is removed by techniques and procedures well known and appreciated by one of ordinary skill in the art, For example, the appropriate thiol protected tricyclic compound of structure (3) wherein Z is —$CH_2$—, —O—, —S—, a bond or —N-Boc is contacted with a molar equivalent of mercuric acetate. The reactants are typically contacted in an appropriate acidic solvent such as trifluoroacetic acid. The reactants are typically stirred together at room temperature for a period of time ranging from 1–24 hours. Mercury is removed from the reaction mixture by the addition of excess hydrogen sulfide. The thiol tricyclic compound of structure (4) wherein Z is —$CH_2$—, —O—, —S—, a bond or —N-Boc is recovered from the reaction zone by extractive methods as is known in the art. It can be purified by silica gel chromatography.

In optional step c, the Boc protecting group on those thiol tricyclic compounds of structure (4) wherein Z is —N-Boc, is removed by techniques and procedures well known and appreciated by one of ordinary skill in the art, such as dilute hydrochloric acid to give the corresponding thiol tricyclic compounds of structure (5) wherein Z is —$NR_4$— wherein $R_4$ is hydrogen.

As summarized in Table 1, the $R_1$ group on the thiol tricyclic compounds of structure (4) and structure (5) can be manipulated using techniques and procedures well known and appreciated by one of ordinary skill in the art.

The thiol functionality of the appropriate thiol tricyclic compound of structure (4) wherein A is —$CH_2$—, —O—, —S— or a bond can be converted to the corresponding pivaloyloxymethyl thioether tricyclic compound of structure (6) wherein A is —$CH_2$—, —O—, —S— or a bond using techniques and procedures well known and appreciated in the art. For example, a pivaloyloxymethyl thioether tricyclic compound of structure (6) wherein Z is —$CH_2$—, —O—, —S— or a bond can be prepared by treating the thiol tricyclic compound of structure (4) wherein A is —$CH_2$—, —O—, —S— or a bond with chloromethyl pivalate in a suitable aprotic solvent, such as dimethylformamide along with a non-nucleophilic base, such as cesium carbonate.

The thiol functionality of the appropriate thiol tricyclic compound of structure (5) wherein Z is —$NR_4$— and $R_4$ is hydrogen is converted to the corresponding pivaloyloxymethyl thioether tricyclic compound of structure (6) wherein Z is —$NR_4$— and $R_4$ is hydrogen with one equivalent of chloromethyl pivalate and one equivalent of a suitable non-nucleophilic base.

The thiol functionality of the appropriate thiol tricyclic compound of structure (4) or (5) can be acylated to give the thioacetate or thiobenzoate tricyclic compounds of structure (7).

For example, the appropriate thiol tricyclic compound of structure (4) or (5) can be contacted with a molar equivalent of an appropriate acylating agent such as acetic anhydride and a catalytic amount of an acid such as sulfuric acid. The reactants are typically stirred together for a period of time ranging from 10 minutes to 10 hours. The thioacetate tricyclic compound of structure (7) can be recovered from the reaction zone by evaporation of the solvent. It can be purified by silica gel chromatography.

Alternatively, the appropriate thiol tricyclic compound of structure (4) or (5) can be contacted with a molar equivalent of an appropriate acylating agent such as benzoyl chloride and a molar equivalent of a base such as pyridine. The reactants are typically stirred together for a period of time ranging from 10 minutes to 10 hours. The thiobenzoate tricyclic compound of structure (7) can be recovered from the reaction zone by evaporation of the solvent. It can be purified by silica gel chromatography.

TABLE 1

| MANIPULATION OF $R_1$ | |
|---|---|
| Compound | $R_1$ |
| 4 and 5 | —H |
| 6 | —$CH_2OCOC(CH_3)_3$ |
| 7 | —$COCH_3$ or —COPh |

The compounds of Formula (I) wherein A is —$NR_4$— wherein $R_4$ is other than hydrogen or wherein A is —$NCOR_5$— can be prepared by techniques and procedures well known and appreciated by one of ordinary skill in the art. A general synthetic procedure for preparing these compounds is set forth in Scheme B. In Scheme B, all substituents unless otherwise indicated are as previously defined.

Scheme B

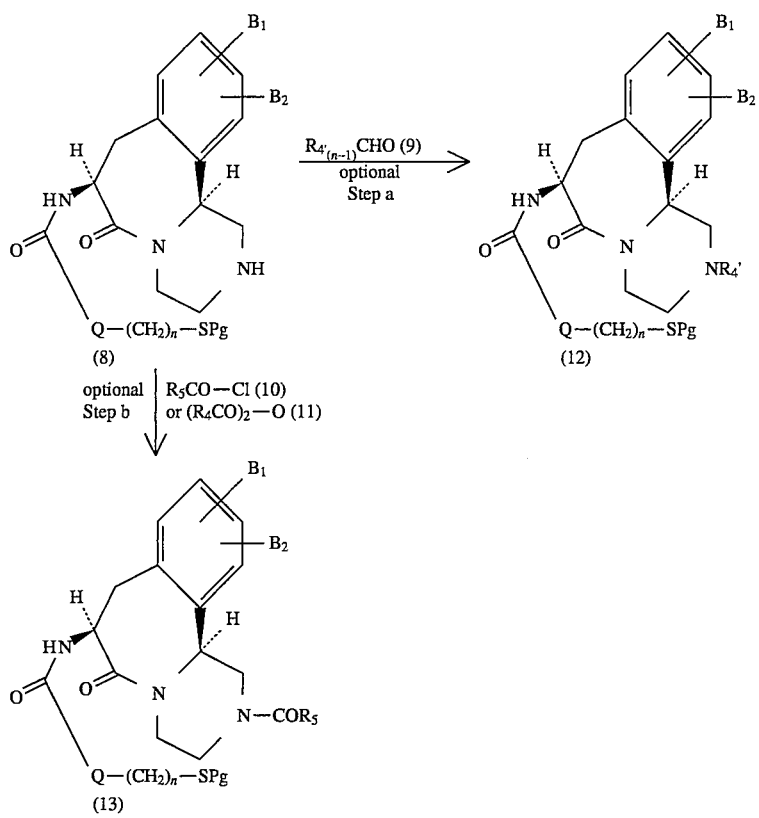

$R_1' = COCH_3$, COPh, $-CH_2OC(O)C(CH_3)_3$ or Pg

In optional step a, the amino functionality of the appropriate thiol protected tricyclic compound of structure (8) wherein A is —NR$_4$— wherein R$_4$ is hydrogen is subjected to reductive alkylation with the appropriate aldehyde of structure (9) using sodium cyanoborohydride, as is well known in the art, to give the corresponding thiol protected N-alkyl tricyclic compound of structure (12).

The thiol protected tricyclic compound of structure (8) wherein Z is —NR$_4$— wherein R$_4$ is hydrogen is prepared by removing the Boc protecting group on those thiol tricyclic compounds of structure (3) wherein A is —N-Boc as described previously in Scheme A, optional step c.

In optional step b, the amino functionality of the appropriate tricyclic compound of structure (8) wherein A is —NR$_4$— wherein R$_4$ is hydrogen is acylated using the appropriate acyl chloride of structure (10) or the appropriate anhydride of structure (11), as is well known in the art, to give the corresponding N-acyl tricyclic compound of structure (13).

The thiol protecting group may be removed as described previously in Scheme A, step b and the R$_1$ group may be manipulated by techniques and procedures well known and appreciated in the art and described previously in Scheme A and shown in Table 1.

Amino tricyclic compounds of structure (1) wherein A is —CH$_2$—, —O—, —S—, a bond or —N-Boc may be prepared as described in Scheme C. In Scheme C, all substituents unless otherwise indicated are as previously defined.

Scheme C

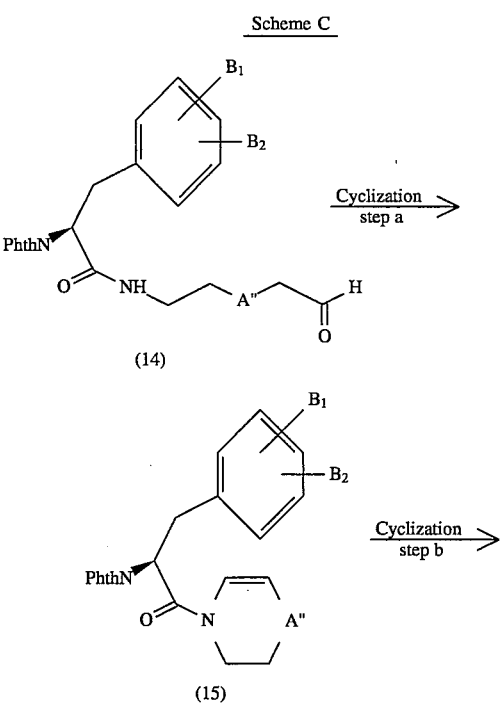

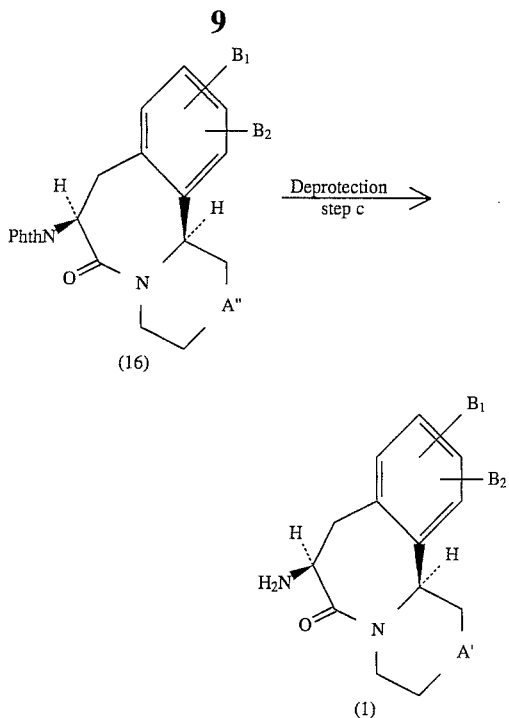

A" = —CH₂—, —O—, —S—, a bond or —NCOCF₃—
A' = —CH₂—, —O—, —S—, a bond or —N—Boc—

In step a, the appropriate aldehyde of structure (14) can be cyclized to the appropriate enamine of structure (15) by acid catalysis. For example, the appropriate aldehyde of structure (14) can be cyclized to the appropriate enamine of structure (15) by treatment with trifluroacetic acid in a suitable aprotic solvent, such as methylene chloride.

In step b, the appropriate enamine of structure (15) can be converted to the corresponding tricyclic compound of structure (16) by an acid catalyzed Friedel-Crafts reaction. For example, the appropriate enamine of structure (15) can be converted to the corresponding tricyclic compound of structure (16) by treatment with a mixture of trifluoromethane sulfonic acid and trifluoroacetic anhydride in a suitable aprotic solvent, such as methylene chloride.

In step c, for those tricyclic compounds of structure (16) wherein A is —CH₂—, —O—, —S— or a bond, the phthalimide protecting group of the appropriate tricyclic compound of structure (16) wherein A is —CH₂—, —O—, —S— or a bond can be removed using techniques and procedures well known in the art. For example, the phthalimide protecting group of the appropriate tricyclic compound of structure (16) wherein A is —CH₂—, —O—, —S— or a bond can be removed using hydrazine monohydrate in a suitable protic solvent such as methanol, to give the corresponding amino tricyclic compound of structure (1) wherein A is —CH₂—, —O—, —S— or a bond.

For those tricyclic compounds of structure (16) wherein A" is —NCOCF₃, the trifluoroacetamide functionality is removed according to the procedure described in *Tetrahedron Letters* 32(28) 3301–3304 1991 to give the corresponding tricyclic compounds of structure (16) wherein A" is —NH. The amino functionality of the appropriate tricyclic compounds of structure (16) wherein A" is —NH is protected with a Boc protecting group by techniques and procedures well known and appreciated in the art to give the corresponding tricyclic compounds of structure (16) wherein A" is —N-Boc. The phthalimide protecting group of the appropriate tricyclic compounds of structure (16) wherein A" is —N-Boc is then removed using hydrazine as described above in step c to give the corresponding amino tricyclic compound of structure (1) wherein A" is —N-Boc.

Starting materials for use in Schemes A through C are readily available to one of ordinary skill in the art.

The following examples present typical syntheses as described in Schemes A through C. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C" refers to degrees Celsius; "mm Hg" refers to millimeters of mercury; "µL" refers to microliters; "µg" refers to micrograms; and "µM" refers to micromolar.

EXAMPLE 1

[4S-[4α, 7α(R*), 12bβ]]-7-[(2-Thio-2-oxoindan)methylamino]-1,2,3,4,5,6,7,8,12b-octahydro-6-oxopyrido[2,1-a][2]benzazepine Scheme C, step a: (R*,R*)]-N-[2-(1,3-Dihydro-1,3-dioxo-2H-isoindol-2-yl)-1-oxo-3-phenylpropyl]-1,2,3,4-tetrahydro-2-pyridine Mix 5-bromo-1-pentene (31.2 g, 0.209 mol) and potassium cyanide (16.8 g, 0.257 mol) in ethylene glycol (85 mL) and heat at 100° C. for 2 hours. Cool, dilute with water (100 mL) and extract into ethyl ether (100 mL). Wash with saturated sodium hydrogen carbonate (35 mL), dry (Na₂SO₄) and distill to give 5-hexenylnitrile as a colorless liquid (16.3 g, 82%); bp 150°–156° C.

Suspend lithium aluminum hydride (6.5 g, 0.17 mol) in ethyl ether (350 mL) and add, by dropwise addition over 30 minutes, 5-hexenylnitrile (16.3 g, 0.171 mol). Stir at room temperature for 2 hours, cool in an ice bath and add sequentially, by very slow addition, water (6.8 mL), 20% sodium hydroxide (5.2 mL), then water (24 mL). Decant the ethereal phase and wash the white salts with ether. Combine the ethereal phases and distill at atm. pressure to give 5-hexenylamine as a colorless liquid (10.7 g, 63%); bp 125°–135° C.

Dissolve 5-hexenylamine (0.88 g, 8.9 mmol) in methylene chloride (50 mL) and treat first with N-phthaloyl-(S)-phenylalanine (2.95 g, 10.0 mmol), then with EEDQ (2.47 g, 10.0 mmol) and stir at room temperature for 6 hours. Evaporate the solvent in vacuo, dissolve the residue in ethyl acetate (75 mL) and wash with 5% sulfuric acid (25 mL), saturated sodium hydrogen carbonate (25 mL) and brine (25 mL). Dry (Na₂SO₄), evaporate the solvent in vacuo and purify by chromatography (hexane/ethyl acetate) to give 2-(1,3-dihydro- 1,3-dioxo-2H-isoindol-2-yl)-1-oxo-3-phenylpropyl-5-hexenylamine as a white solid (1.8 g, 55%).

Dissolve 2-(1,3-dihydro-1,3-dioxo-2H-isoindol-2-yl)-1-oxo-3-phenylpropyl-5-hexenylamine (1.2 g, 3.19 mmol) in methylene chloride (40 mL) and methanol (4 mL) and cool to −78° C. under a nitrogen atmosphere. Treat with ozone until a blue color persists, degas with nitrogen for 20 minutes and add pyridine (0.2 mL). Quench with dimethylsulfide (4 mL) and stir overnight at room temperature. Dilute with methylene chloride (75 mL) and wash with 5% sulfuric acid (40 mL) and brine (40 mL) . Dry (Na₂SO₄), evaporate the solvent in vacuo and purify by chromatography (hexane/ethyl acetate) to give 2-(1,3-dihydro-1,3-dioxo-2H-isoindol-2-yl)-1-oxo-3-phenylpropyl-5-oxo-pentylamine as a white solid (972 mg, 80%).

Dissolve 2-(1,3-dihydro-1,3-dioxo-2H-isoindol-2-yl)-1-oxo-3-phenylpropyl-5-oxo-pentylamine (153 mg, 0.404 mmol) in anhydrous methylene chloride (7 mL) and treat with trifluoroacetic acid (0.04 mL, 0.5 mmol). Stir at room temperature for 3 hours, partition between methylene chloride (25 mL) and saturated sodium hydrogen carbonate (15 mL). Dry ($Na_2SO_4$), evaporate the solvent in vacuo and purify by chromatography (hexane/ethyl acetate) to give the title compound as a white solid (623 mg, 83%).

Scheme C, step b: [4α, 7α(R*), 12bβ]-7-[(1,3-Dihydro-1, 3-dioxo-2H-isoindol-2-yl)]-1,2,3,4,6,7,8,12b-octahydro-6-oxopyrido[2,1-a][2]benzazepine Dissolve (R*,R*)]-N-[2-(1,3-dihydro-1,3-dioxo-2H-isoindol-2-yl)-1-oxo-3-phenylpropyl]-1,2,3,4-tetrahydro-2-pyridine (623 mg, 1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL). Dry ($Na_2SO_4$), evaporate the solvent in vacuo and purify by chromatography (hexane/ethyl acetate) to give the title compound as a white solid (600 mg, 96%).

Scheme C, step c: [4α, 7α(R*), 12bβ]-7-(Amino)-1,2,3,4, 6,7,8,12b-octahydro-6-oxopyrido[2,1-a][2]benzazepine Dissolve [4α, 7α(R*), 12bβ]-7-[(1,3-dihydro-1,3-dioxo-2H-isoindol-2-yl)]-1,2,3,4,6,7,8,12b-octahydro-6-oxopyrido[2,1-a][2]benzazepine (669 mg, 1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and $MgSO_4$ and evaporate the solvent in vacuo to give the title compound as a white solid (407 mg, 95%).

Scheme A, step a: [4S-[4α, 7α(R*), 12bβ]]-7-[(2-(4-Methoxybenzylthio)-2-oxoindan)methylamino]1,2,3,4,6,7,8,12b-octahydro-6-oxopyrido[2,1-a][2]benzazepine Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add α,α'-dibromo-o-xylene (26.4 g, 0.1 00 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 2,2-(dicarboethoxy)indan as a pale yellow oil (16.0 g, 61.5%).

Dissolve 2,2-(dicarboethoxy)indan (15.9 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry ($MgSO_4$) and pass through a silica gel plug to give 2-(carboethoxy)indan as an amber oil (6.49 g, 56%).

Dissolve 2-(carboethoxy)indan (6.49 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1.

Extract with methylene chloride (2×150 mL), dry ($Na_2SO_4$) and evaporate the solvent in vacuo to give 2-indancarboxylic acid as a tan solid (3.82 g, 69%).

Dissolve 2-indancarboxylic acid (3.82 g, 23.5 mmol) in methanol (60 mL) and treat with dimethoxypropane (5.8 mL, 47 mmol) and sulfuric acid (0.8 mL). Stir at room temperature for 6 days. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry ($Na_2SO_4$). Evaporate the solvent in vacuo and pass through a plug of silica gel to give 2-(carbomethoxy)indan as a yellow oil (3.98 g, 96%).

Mix 4-methoxybenzylthiol (3.0 g, 19 mmol) in sodium hydroxide (20 mL of a 2.5N aqueous solution) and methanol (10 mL). Add saturated aqueous copper sulfate solution (1.5 mL) and stir at room temperature for 2 hours, blowing air over the top of the mixture. Filter the solid, wash with water and dry to give 4-methoxybenzyl disulfide as a pale yellow powder (2.71 g, 91%).

Cool lithium hexamethyldisilazane (4.2 mL, 4.2 mol, 1.0M in tetrahydrofuran) to −78° C. and treat with a solution of 2-(carbomethoxy)indan (625 mg, 3.55 mmol) in tetrahydrofuran (5 mL). Stir for 1 hour add hexamethylphosphoramide (0.93 mL, 5.3 mmol) and stir for 5 minutes. Add 4-methoxybenzyl disulfide (1.6 g, 5.2 mmol) in tetrahydrofuran (10 mL). Stir for 5 hours at −78° C. and quench with a solution of ammonium chloride. Partition between ethyl acetate (75 mL) and brine (30 mL). Dry ($Na_2SO_4$), evaporate the solvent in vacuo and purify by silica gel chromatography (4:1 hexane/ethyl acetate) to give 2-(carbomethoxy)-2-(4-methoxybenzylthio)indan (2.20 g).

Dissolve 2-(carbomethoxy)-2-(4-methoxybenzylthio)indan (2.20 g, 3.55 mmol) in 95% ethanol (25 mL), water (12 mL) and tetrahydrofuran (15 mL). Treat with potassium hydroxide (1.3 g, 23 mmol) and stir at room temperature for 1 hour. Filter and evaporate the solvent in vacuo. Partition between water (125 mL) and ether (75 mL). Separate the aqueous phase and acidify with cold concentrated hydrochloric acid. Extract with methylene chloride (75 mL), dry ($Na_2SO_4$) and evaporate the solvent in vacuo. Purify by silica gel chromatography (2:1 hexane/ethyl acetate) to give 2-carboxy-2-(4-methoxybenzylthio)indan as a yellow solid (0.48 g, 43%).

Dissolve [4α, 7α(R*), 12bβ]-7-(amino)-1,2,3,4,6,7,8, 12b-octahydro-6-oxopyrido[2,1-a][2]benzazepine (136 mg, 0.59 mmol) and EDC (170 mg, 0.886 mmol) in tetrahydrofuran (5 mL). Treat with 2-carboxy-2-(4-methoxybenzylthio)indan (232 mg, 0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry ($Na_2SO_4$) and evaporate the solvent in vacuo. Purify by silica gel chromatography (2:1 hexane/ethyl acetate to 3:2 hexane/ethyl acetate) to give the title compound as a pale yellow foam (205 mg, 65.9%).

Scheme A, step b: [4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine Dissolve [4S-[4α, 7α(R*), 12bβ]]-7-[(2-(4-methoxybenzylthio)- 2-oxoindan)methylamino]-1,2,3,4,6,7,8,12b-octahydro-6-oxopyrido[2,1-a] [2]benzazepine[(200 mg, 0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry ($Na_2SO_4$) and evaporate the solvent in vacuo. Purify by silica gel chromatography (3:2 hexane/ethyl acetate) to give the title compound (128 mg, 83%).

EXAMPLE 2

[4S-[4α, 7α(R*), 12bβ]]-7-[(2-Acetylthio-2-oxoindan)methylamino]-1,2,3,4,6,7,8,12b-octahydro-6-oxopyrido[2,1-a][2]benzazepine Place [4S-[4α, 7α(R*), 12bβ]]-7-[(2-thio-2-oxoindan)methylamino]-1,2,3,4,6,7,8,12b-octahydro-6-oxopyrido[2,1-a][2]benzazepine (256 mg, 0.63 mmol) in a reaction flask and treat sequentially with acetic anhydride (0.08 mL, 0.85 mmol) and 10% sulfuric acid in acetic acid (0.01 mL). Add methylene chloride (2 mL) and stir for 20 hours. Partition between ether (75 mL) and saturated sodium hydrogen carbonate (25 mL). Separate the organic phase, dry ($Na_2SO_4$) and evaporate the solvent in vacuo. Purify by chromatography (3:2 hexane/ethyl acetate) to give the title compound as a tan solid (261 mg, 92%).

EXAMPLE 3

[4S-[4α, 7α(R*), 12bβ]]-7-[(2-(2-Mercaptoethyl)-2-oxoindan)methylamino]-1,2,3,4,6,7,8,12b-octahydro-6-oxopyrido[2,1-a][2]benzazepine Scheme A, step a: [4S-[4α, 7α(R*), 12bβ]]-7-[(2-[2-(4-Methoxybenzylthio)ethane-2-oxoindan)methylamino]-1,2,3,4,6,7,8,12b-octahydro-6-oxopyrido[2,1-a][2]benzazepine Cool lithium hexamethyldisilazane (4.2 mL 4.2 mmol) in a dry ice/acetone bath and add, by dropwise addition, a solution of 2-(carbomethoxy)indane (625 mg, 3.55 mmol) in tetrahydrofuran (6 mL). Stir for 30 minutes then add hexamethylphosphoramide (1.0 mL, 5.7 mmol). Stir for 45 minutes then add 1-bromo-2-chloroethane (0.37 mL, 4.44 mmol). Stir for 3 hours, remove the ice bath and allow to warm to room temperature. Quench with aqueous ammonium chloride (30 mL) and extract with ethyl acetate (75 mL). Dry ($Na_2SO_4$) and evaporate the solvent in vacuo. Pass through a plug of silica gel (6:1 hexane/ethyl acetate) to give 2-(carbomethoxy)-2-(2-chloroethane)indane (0.62 g).

Dissolve 4-methoxybenzylthiol (0.7 mL, 5 mmol) in tetrahydrofuran (10 mL) and place under an argon atmosphere. Treat with sodium hydride (144 mg of an 80% dispersion in mineral oil, 4.8 mmol). Stir the suspension for 10 minutes and add tetrabutylammonium iodide (40 mg, 0.11 mmol). Stir for 10 minutes then add a solution of 2-(carbomethoxy)-2-(2-chloroethane)indane (0.6 g, 3.55 mmol) in tetrahydrofuran (5 mL). Stir for 18 hours and partition between aqueous ammonium chloride (15 mL) and ethyl acetate (50 mL). Dry ($Na_2SO_4$) and evaporate the solvent in vacuo. Purify by silica gel chromatography (6:1 hexane/ethyl acetate) to give 2-(carbomethoxy)-2-[2-(4-methoxybenzylthio)ethane]indan (0.75 g).

Dissolve 2-(carbomethoxy)-2-[2-(4-methoxybenzylthio)ethane]indan (0.75 g, 3.55 mmol) in 95% ethanol (16 mL), water (8 mL) and tetrahydrofuran (10 mL). Treat with potassium hydroxide (1.3 g, 23 mmol). Stir for 1 hour and evaporate the solvent in vacuo. Partition between water (50 mL) and ethyl ether (2×35 mL). Cool the aqueous phase in an ice bath and acidify with concentrated hydrochloric acid to pH 1. Extract with methylene chloride (75 mL), dry ($Na_2SO_4$) and evaporate the solvent in vacuo to give 2-carboxy-2-[2-(4-methoxybenzylthio)ethane]indan as a white solid (147 mg).

Dissolve [4α, 7α(R*), 12bβ]-7-(amino)-1,2,3,4,6,7,8,12b-octahydro-6-oxopyrido[2,1-a][2]benzazepine (136 mg, 0.59 mmol) and EDC (170 mg, 0.886 mmol) in tetrahydrofuran (5 mL). Treat with 2-carboxy-2-[2-(4-methoxybenzylthio)ethane]indan (0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry ($Na_2SO_4$) and evaporate the solvent in vacuo. Purify by silica gel chromatography to give the title compound.

Scheme A, step b: [4S-[4α, 7α(R*), 12bβ]]-7-[(2-92-Mercaptoethyl)-2-oxoindan)methylamino]-1,2,3,4,6,7,8,12b-octahydro-6-oxopyrido[2,1-a][2]benzazepine Dissolve [4S-[4α, 7α(R*), 12bβ]]-7-[(2-[2-(4-methoxybenzylthio)ethane-2-oxoindan)methylamino]-1,2,3,4,6,7,8,12b-octahydro-6-oxopyrido[2,1-a][2]benzazepine (0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry ($Na_2SO_4$) and evaporate the solvent in vacuo. Purify by silica gel chromatography to give the title compound.

EXAMPLE 4

[4S-[4α, 7α(R*), 12bβ]]-7-[(2-Mercaptomethyl-2-oxoindan)methylamino]-1,2,3,4,6,7,8,12b-octahydro-6-oxopyrido[2,1-a][2]benzazepine Scheme A, step a: [4S-[4α, 7α(R*), 12bβ]]-7-[(2-(t-butylthio)methane-2-oxoindan)methylamino]-1,2,3,4,6,7,8,12b-octahydro-6-oxopyrido[2,1-a][2]benzazepine Dissolve diethyl malonate (7.6 mL, 50 mmol) in anhydrous tetrahydrofuran (500 mL) and place under an argon atmosphere. Cool to 5° C., add sodium hydride (1.2 g, 50 mmol) and stir briefly until homogeneous. Add α,α'-dibromo-o-xylene (13.2 g, 50 mmol) and stir an additional 15 minutes. Add additional sodium hydride (1.2 g, 50 mmol) and stir for 16 hours while warming to room temperature. Filter, evaporate the solvent in vacuo and purify by silica gel chromatography (1:1 methylene chloride/hexane) to give 2,2-dicarboethoxy-indan (9.64 g, 74%).

Dissolve 2,2-dicarboethoxy-indan (5.67 g, 21.7 mmol) in ethanol (150 mL). Add 1N lithium hydroxide (50 mL) and stir overnight at room temperature. Reflux for 1 hour and concentrate the solution in vacuo. Partition between ethyl acetate and 6N hydrochloric acid. Separate the organic phase and wash with brine. Dry ($MgSO_4$) and evaporate the solvent in vacuo to give an off-white solid. Distill (120°–160° C. @ 0.2–0.5 mmHg) to give 2-carboxy-indan (2.5 g, 71%).

Dissolve 2-carboxy-indan (2.5 g, 15.4 mmol) in methanol and cool to 0° C. Saturate with hydrochloride gas then add 2,2-dimethoxypropane (2–3 mL). Stir overnight then evaporate the solvent in vacuo. Purify by silica gel chromatography (2:1 methylene chloride/hexane) to give 2-carbomethoxy-indan as a water white oil. (2.04 g, 75%).

Dissolve diisopropylamine (i.90 mL, 7.8 mmol) in anhydrous tetrahydrofuran (8 mL), cool to −20° C. and place under an argon atmosphere. Add, by dropwise addition, n-butyllithium (3.12 mL of a 2.5N solution in hexanes, 7.8 mmol) and stir for 20 minutes while cooling to −70° C. Add, by dropwise addition, a solution of 2-carbomethoxy-indan (1.34 g, 7.8 mmol) in anhydrous tetrahydrofuran (8 mL). Stir at −70° C. for an additional 30 minutes then add trimethylsilyl chloride (freshly distilled from barium oxide, 1.0 mL, 7.8 mmol). Allow to warm to 10° C., evaporate the solvent in vacuo and dry the residue under vacuum for 30 minutes. Suspend the residue in methylene chloride (30 mL), add zinc bromide (300 mg, 1.3 mmol) followed by t-butyl chloromethylsulfide (1.08 g, 7.8 mmol). Stir for 15 minutes at room temperature and add additional zinc bromide (500 mg, 2.2 mmol). Pour onto excess saturated sodium hydrogen carbonate and shake vigorously. Separate the organic phase and extract the aqueous phase with methylene chloride (30 mL). Combine the organic phases, dry ($MgSO_4$) and evaporate the solvent in vacuo to give crude product as a brown oil (2.12 g, 98%). Purify by silica gel chromatography (30°–70° C. methylene chloride/hexane) and recrystallize (methanol) to give 2-carbomethoxy-2-(t-butyl)thiomethyl-indan as a crystalline solid (1.3 g, 61%).

Dissolve 2-carbomethoxy-2-(t-butyl)thiomethyl-indan (557 mg, 2.0 mmol) in methanol (15 mL) and add 1N lithium hydroxide (3.5 mL). Warm briefly to effect solution then stir at room temperature under an argon atmosphere for 1 hour. Reflux for 6 hours, concentrate in vacuo to a volume of 3 mL and dilute to a volume of 15 mL with water. Wash with methylene chloride and acidify and aqueous phase with excess 2N hydrochloric acid. After 5 minutes, collect the resulting white precipitate by filtration and dry to give 2-carboxy-2-(t-butyl)thiomethyl-indan (506 mg, 96%); mp 158°–163° C.

Dissolve [4α, 7α(R*), 12bβ]-7-(amino)-1,2,3,4,6,7,8,12b-octahydro-6-oxopyrido[2,1-a][2]benzazepine (136 mg, 0.59 mmol) and EDC (170 mg, 0.886 mmol) in tetrahydrofuran (5 mL). Treat with 2-carboxy-2-(t-butyl)thiomethyl-indan (0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry ($Na_2SO_4$) and evaporate the solvent in vacuo. Purify by silica gel chromatography to give the title compound.

Scheme A, step b: [4S-[4α, 7α(R*), 12bβ]]-7-[(2-Mercaptomethyl-2-oxoindan)methylamino]1,2,3,4,6,7,8,12b-octahydro-6-oxopyrido[2,1-a][2]benzazepine Dissolve [4S-[4α, 7α(R*), 12bβ]]-7-[(2-(t-butylthio)methane- 2-oxoindan)methylamino]-1,2,3,4,6,7,8,12b-octahydro-6-oxopyrido[2,1-a][2]benzazepine (0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry ($Na_2SO_4$) and evaporate the solvent in vacuo. Purify by silica gel chromatography to give the title compound.

EXAMPLE 5

[4S-[4α, 7α(R*), 12bβ]]-7-[(1-Thio-1-oxocyclopentane)methylamino]-1,2,3,4,6,7,8,12b-octahydro-6-oxopyrido[2,1-a][2] benzazepine Scheme A, step a: [4S-[4α, 7α(R*), 12bβ]],7-[(1-(4-methoxybenzylthio)-1-oxo-cyclopentane)methylamino]-1,2,3,4,6,7,8,12b-octahydro-6-oxopyrido[2,1-a][2]benzazepine Dissolve diisopropylamine (0.46 mL, 3.3 mmol) in tetrahydrofuran (10 mL) and cool in an ice bath. Add, by dropwise addition, n-butyllithium (1.8 mL of a 1.6M solution in hexanes, 2.9 mmol). Stir for 15 minutes, cool to −78° C. and add a solution of methyl cyclopentanecarboxylate (322 mg, 2.51 mmol) in tetrahydrofuran (5 mL). Stir for 1 hour then treat with hexamethylphosphoramide (0.66 mL, 3.8 mmol). Stir for 15 minutes then add 4-methoxybenzyl disulfide ( (1.0 g, 3.3 mmol) in tetrahydrofuran (13 mL). Stir for 3 hours at −78° C., quench with saturated aqueous ammonium chloride (5 mL). Partition between water (2×50 mL) and ethyl acetate (100 mL). Dry ($Na_2SO_4$) and pass through a plug of silica gel (methylene chloride) to give 1-(carbomethoxy)-1-(4-methoxybenzylthio)cyclopentane as a pale yellow oil.

Dissolve 1-(carbomethoxy)-1-(4-methoxylbenzylthio)cyclopentane (3.3 mmol) in 95% ethanol (18 mL), water (9 mL), and tetrahydrofuran (10 mL). Treat with potassium hydroxide (0.91 g, 16 mmol). Stir at room temperature for 2 hours and evaporate the solvent in vacuo. Partition between water (50 mL) and ethyl ether (30 mL). Acidify the aqueous phase with cold concentrated hydrochloric acid and extract with methylene chloride (50 mL). Dry ($MgSO_4$) and evaporate the solvent in vacuo to give 1-(carboxy)-1-(4-methoxybenzylthio)cyclopentane as a pale yellow oil (483 mg, 72%).

Dissolve [4α, 7α(R*), 12b8]-7-(amino)-1,2,3,4,6,7,8, 12b-octahydro-6-oxopyrido[2,1-a][2]benzazepine (136 mg, 0.59 mmol) and EDC (170 mg, 0.886 mmol) in tetrahydrofuran (5 mL). Treat with 1-(carboxy)-1-(4-methoxybenzylthio)cyclopentane (0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry ($Na_2SO_4$) and evaporate the solvent in vacuo. Purify by silica gel chromatography to give the title compound.

Scheme A, step b: [4S-[4α, 7α(R*), 12bβ]]-7-[(1-Thio-1-oxocyclopentane)methylamino]-1,2,3,4,6,7,8,12b-octahydro-6-oxopyrido[2,1-a][2]benzazepine Dissolve [4S-[4α, 7α(R*), 12bβ]]-7-[(1-(4-methoxybenzylthio)-1-oxo-cyclopentane)methylamino]-1,2,3,4,6,7,8, 12b-octahydro-6-oxopyrido[2,1-a][2]benzazepine (0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry ($Na_2SO_4$) and evaporate the solvent in vacuo. Purify by silica gel chromatography to give the title compound.

EXAMPLE 6

[4S-[4α, 7α(R*), 12bβ]]-7-[(5-Thio-5-oxo-4,5-dihydro-cyclopentimidazole)methylamino]3,4,6,7,8,12b-hexahydro-6-oxo-1H-[1,4]-oxazino[3,4-a][2] benzazepine Scheme C, step a: (R*,R*)]-N-[2-(1,3-Dihydro-1,3-dioxo-2H-isoindol-2-yl)-1-oxo-3-phenylpropyl]-3,4-dihydro-2H-1,4-oxazine Wash sodium hydride (7.75 g, 191 mmol of a 59% dispersion in paraffin) 2 times with dry hexane (2×) under a nitrogen atmosphere. Add anhydrous dimethylformamide (90 mL) and cool with an ice/methanol bath. Add, by portion wise addition, ethanolamine hydrochloride (96.7 mmol), stir for 5 minutes and add potassium iodide (5.2 g, 32 mmol). Add, by dropwise addition, bromoacetaldehyde diethylacetal (14.5 mL, 96.7 mmol), remove the ice bath and stir for 8 hours at room temperature. Add the mixture to a solution of N-phthaloyl-(S)-phenylalanine (14.2 g, 48 mmol) and N-carbethoxy-2-ethoxy-1,2-dihydroquinoline (11.9 g, 48 mmol) in anhydrous tetrahydrofuran (40 mL). Stir for 18 hours at room temperature, partition between water (200 mL) and diethyl ether (200 mL) and separate the organic phase. Extract the aqueous phase with diethyl ether (200 mL), combine the organic phases and wash with 1N hydrochloric acid (2×200 mL), then saturated sodium hydrogen carbonate (2×200 mL), then brine (50 mL). Dry (MgSO$_4$), filter and evaporate the solvent in vacuo to give the intermediate acetal.

Dissolve the intermediate acetal (30.3 mmol) in chloroform (500 mL) and add trifluoroacetic acid (4.5 mL). Reflux for 4 hours under a nitrogen atmosphere, cool and wash with saturated sodium hydrogen carbonate (300 mL) and filter through anhydrous MgSO$_4$. Evaporate the solvent in vacuo and purify by chromatography to give the title compound.

Scheme C, step b: [4α, 7α(R*), 12bβ]-7-[(1,3-Dihydro-1,3-dioxo-2H-isoindol-2-yl)]-3,4,6,7,8,12b-hexahydro-6-oxo-1H-[1,4]-oxazino[3,4-a][2]benzazepine Dissolve (R*,R*)]-N-[2-(1,3-Dihydro-1,3-dioxo-2H-isoindol-2-yl)- 1-oxo-3-phenylpropyl]-3,4-dihydro-2H-1,4-oxazine (1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL), dry (Na$_2$SO$_4$), evaporate the solvent in vacuo and purify by chromatography to give the title compound.

Scheme C, step c: [4α, 7α(R*), 12bβ]-7-(Amino)-3,4,6,7,8,12b-hexahydro-6-oxo-1H-[1,4]-oxazino[3,4-a][2]benzazepine Dissolve [4α, 7α(R*), 12bβ]-7-[(1,3-dihydro-1,3-dioxo-2H-isoindol-2-yl)]-3,4,6,7,8,12b-hexahydro-6-oxo-1H-[1,4]-oxazino[3,4-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO$_4$ and evaporate the solvent in vacuo to give the title compound.

Scheme A, step a: [4S-[4α, 7α(R*), 12bβ]]-7-[(5-(4-methoxybenzylthio)-5-oxo-1-(carbo-t-butyloxy)-4,5-dihydro-cyclopentimidazole)methylamino]-3,4,6,7,8,12b-hexahydro-6-oxo-1H-[1,4]-oxazino[3,4-a][2]benzazepine Dissolve 4,5-imidazoledicarboxylic acid (31.2 g, 0.2 mol) in ethanol (500 mL) and treat with concentrated sulfuric acid (0.5 mL). Heat to 60° C. for 16 hours, cool and reduce the solvent by 50% in vacuo. Dilute with ethyl ether (500 mL), wash with saturated sodium hydrogen carbonate, then brine. Dry (MgSO$_4$) and evaporate the solvent in vacuo to give 4,5-(dicarboethoxy)imidazole.

Dissolve 4,5-(dicarboethoxy)imidazole (1.06 g, 5 mmol) and triethylamine (1.5 mL, 7.5 mmol) in 50/50 dioxane water (25 mL). Add [2-(tert-butyloxycarbonyloxyimino)-2-phenylacetonitrile] (1.36 g, 5.5 mmol) and stir at room temperature for 2 hours. Add water (7.5 mL) and ethyl acetate (10 mL), separate the aqueous phase and wash with ethyl acetate (10 mL). Combine the organic phases, dry (MgSO$_4$) and evaporate the solvent in vacuo. Purify the residue by silica gel chromatography to give N-(carbo-t-butyloxy)-4,5-(dicarboethoxy)imidazole.

Dissolve N-(carbo-t-butyloxy)-4,5-(dicarboethoxy)imidazole (3.12 g, 10 mmol) in anhydrous tetrahydrofuran (30 mL) and cool to −20° C. Treat with lithium borohydride (7 mL of a 2N solution) and stir under a nitrogen atmosphere for several days. Carefully add water and partition between ethyl acetate and 5% hydrochloric acid. Separate the organic phase, wash with brine and dry (MgSO$_4$). Evaporate the solvent in vacuo and purify by silica gel chromatography to give N-(carbo-t-butyloxy)-4,5-(dihydroxymethyl)imidazole.

Dissolve N-bromosuccinimide (1.78 g, 0.01 mol) in tetrahydrofuran (60 mL) and add a solution of triphenylphosphine (2.62 g, 0.01 mol) in tetrahydrofuran. Add a solution of N-(carbo-t-butyloxy)-4,5-(dihydroxymethyl)imidazole (1.14 g, 5 mmol) in tetrahydrofuran (25 mL) and stir until most of the solid goes into solution. Evaporate the solvent in vacuo and partition the residue between water and ethyl ether. Separate the organic phase and wash with water. Dry (Na$_2$SO$_4$) and evaporate the solvent in vacuo. Purify by silica gel chromatography to give N-(carbo-t-butyloxy)-4,5-(dibromomethyl)imidazole.

Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add N-(carbo-t-butyloxy)-4,5-(dibromomethyl)imidazole (35.4 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 5,5-(dicarboethoxy)-1-(carbo-t-butyloxy)-4,5-dihydro-cyclopentimidazole.

Dissolve 5,5-(dicarboethoxy)-1-(carbo-t-butyloxy)-4,5-dihydro-cyclopentimidazole (21.3 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry (Mg$_s$O$_4$) and pass through a silica gel plug to give 5-(carboethoxy)-1-(carbo-t-butyloxy)-4,5-dihydro-cyclopentimidazole.

Dissolve 5-(carboethoxy)-1-(carbo-t-butyloxy)-4,5-dihydro-cyclopentimidazole (9.5 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry (Na$_2$SO$_4$) and evaporate the solvent in vacuo to give 5-(carboxy)-1-(carbo-t-butyloxy)-4,5-dihydro-cyclopentimidazole.

Dissolve 5-(carboxy)-1-(carbo-t-butyloxy)-4,5-dihydro-cyclopentimidazole (5.9 g, 23.5 mmol) in methanol (60 mL) and treat with dimethoxypropane (5.8 mL, 47 mmol) and sulfuric acid (0.8 mL). Stir at room temperature for 1 day. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry (Na$_2$SO$_4$). Evaporate the solvent in vacuo and pass through a plug of silica gel to give 5-(carbomethoxy)-1-(carbo-t-butyloxy)-4,5-dihydro-cyclopentimidazole.

Mix 4-methoxybenzylthiol (3.0 g, 19 mmol) in sodium hydroxide (20 mL of a 2.5N aqueous solution) and methanol (10 mL). Add saturated aqueous copper sulfate solution (1.5 mL) and stir at room temperature for 2 hours, blowing air over the top of the mixture. Filter, wash solid with water and dry to give 4-methoxybenzyl disulfide as a pale yellow powder (2.71 g, 91%).

Cool lithium hexamethyldisilazane (4.2 mL, 4.2 mol, 1.0M in tetrahydrofuran) to −78° C. and treat with a solution of 5-(carbomethoxy)-1-(carbo-t-butyloxy)-4,5-dihydro-cyclopentimidazole (944 mg, 3.55 mmol) in tetrahydrofuran (5 mL). Stir for 1 hour then add hexamethylphosphoramide (0.93 mL, 5.3 mmol) and stir for 5 minutes. Add 4-methoxybenzyl disulfide (1.6 g, 5.2 mmol) in tetrahydrofuran (10 mL). Stir for 5 hours at −78° C. and quench with a solution of ammonium chloride. Partition between ethyl acetate (75 mL) and brine (30 mL). Dry (Na$_2$SO$_4$), evaporate the solvent in vacuo and purify by silica gel chromatography to give 5-(carbomethoxy)-1-(carbo-t-butyloxy)-5-(4-methoxybenzylthio)-4,5-dihydro-cyclopentimidazole.

Dissolve 5-(carbomethoxy)-1-(carbo-t-butyloxy)-5-(4-methoxybenzylthio)-4,5-dihydro-cyclopentimidazole (1.43 g, 3.55 mmol) in 95% ethanol (25 mL), water (12 mL) and tetrahydrofuran (15 mL). Treat with potassium hydroxide (1.3 g, 23 mmol) and stir at room temperature for 1 hour. Filter and evaporate the solvent in vacuo. Partition between water (125 mL) and ether (75 mL). Separate the aqueous phase and acidify with cold concentrated hydrochloric acid. Extract with methylene chloride (75 mL), dry (Na$_2$SO$_4$) and evaporate the solvent in vacuo. Purify by silica gel chromatography to give 5-(carboxy)-1-(carbo-t-butyloxy)-5-(4-methoxybenzylthio)-4,5-dihydro-cyclopentimidazole.

Dissolve [4α, 7α(R*), 12bβ]-7-(amino)-1,2,3,4,6,7,8, 12b-octahydro-6-oxopyrido[2,1-a][2]benzazepine (136 mg, 0.59 mmol) and EDC (170 mg, 0.886 mmol) in tetrahydrofuran (5 mL). Treat with 5-(carboxy)-1-(carbo-t-butyloxy)-5-(4-methoxybenzylthio)-4,5-dihydro-cyclopentimidazole (0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry (Na$_2$SO$_4$) and evaporate the solvent in vacuo. Purify by silica gel chromatography to give the title compound.

Scheme A, step b: [4S-[4α, 7α(R*), 12bβ]]-7-[(5-Thio-5-oxo-4,5-dihydro-cyclopentimidazole)methylamino]-3,4,6,7, 8,12b-hexahydro-6-oxo-1H-[1,4]-oxazino[3,4-a][2]benzazepine Dissolve [4S-[4α, 7α(R*), 12bβ]]-7-[(5-(4-methoxybenzylthio)-5-oxo-1-(carbo-t-butyloxy)-4,5-dihydro-cyclopentimidazole)methylamino]-3,4,6,7,8,12b-hexahydro-6-oxo-1H-[1,4]-oxazino[3,4-a][2]benzazepine (0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry (Na$_2$SO$_4$) and evaporate the solvent in vacuo. Purify by silica gel chromatography to give the title compound.

EXAMPLE 7

Preparation of [4S-[4α, 7α(R*), 12bβ]]-7-[(5-Thio-5-oxo-4,5,6-trihydro-cyclopenta[c] furan)methylamino]-3,4,6,7,8,12b-hexahydro-6-oxo-1H-[1,4]-thiazino[3,4-a][2]benzazepine Scheme C, step a: (R*,R*)]-N-[2-(1,3-Dihydro-1,3-dioxo-2H-isoindol-2-yl)-1-oxo-3-phenylpropyl]-3,4-dihydro-2H-1,4-thiazine Wash sodium hydride (7.75 g, 191 mmol of a 59% dispersion in paraffin) 2 times with dry hexane (2×) under a nitrogen atmosphere. Add anhydrous dimethylformamide (90 mL) and cool with an ice/methanol bath. Add, by portionwise addition, 2-aminoethanethiol hydrochloride (96.7 mmol), stir for 5 minutes and add potassium iodide (5.2 g, 32 mmol). Add, by dropwise addition, bromoacetaldehyde diethylacetal (14.5 mL, 96.7 mmol), remove the ice bath and stir for 8 hours at room temperature. Add to a solution of N-phthaloyl-(S)-phenylalanine (14.2 g, 48 mmol) and N-carbethoxy-2-ethoxy-1, 2-dihydroquinoline (11.9 g, 48 mmol) in anhydrous tetrahydrofuran (40 mL). Stir for 18 hours at room temperature, partition between water (200 mL) and diethyl ether (200 mL) and separate the organic phase. Extract the aqueous phase with diethyl ether (200 mL), combine the organic phases and wash with 1N hydrochloric acid (2×200 mL), then saturated sodium hydrogen carbonate (2×200 mL), then brine (50 mL). Dry (MgSO$_4$), filter and evaporate the solvent in vacuo to give the intermediate acetal.

Dissolve the intermediate acetal (30.3mmol) in chloroform (500 mL) and add trifluoroacetic acid (4.5 mL). Reflux for 4 hours under a nitrogen atmosphere, cool and wash with saturated sodium hydrogen carbonate (300 mL) and filter through anhydrous MgSO$_4$. Evaporate the solvent in vacuo and purify by chromatography to give the title compound.

Scheme C, step b: [4α, 7α(R*), 12bβ]-7-[(1,3-Dihydro-1, 3-dioxo-2H-isoindol-2-yl)]-3,4,6,7,8,12b-hexahydro-6-oxo-1H-[1,4]-thiazino[3,4-a][2]benzazepine Dissolve (R*,R*)]-N-[2-(1,3-Dihydro-1,3-dioxo-2H-isoindol-2-yl)-1-oxo-3-phenylpropyl]-3,4-dihydro-2H-1,4-thiazine (1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL), dry (Na$_2$SO$_4$), evaporate the solvent in vacuo and purify by chromatography to give the title compound.

Scheme C, step c: [4α, 7α(R*), 12bβ]-7-(Amino)-3,4,6,7, 8,12b-hexahydro-6-oxo-1H-[1,4]-thiazino[3,4-a][2]benzazepine Dissolve [4α, 7α(R*), 12bβ]-7-[(1,3-dihydro-1,3-dioxo-2H-isoindol-2-yl)]-3,4,6,7,8,12b-hexahydro-6-oxo-1H-[1,4]-thiazino[3,4-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO$_4$ and evaporate the solvent in vacuo to give the title compound.

Scheme A, step a: [4S-[4α, 7α(R*), 12bβ]]-7-[(5-(4-methoxybenzylthio)-5-oxo-2,4,5,6-tetrahydro-cyclopenta[c] furan)methylamino]-3,4,6,7,8,12b-hexahydro-6-oxo-1H-[1, 4]-thiazino[3,4-a][2]benzazepine Dissolve 3,4-(dicarboethoxy)furan (21.2 g, 10 mmol) in anhydrous tetrahydrofuran (30 mL) and cool to −20° C. Treat with lithium borohydride (7 mL of a 2N solution) and stir under a nitrogen atmosphere for several days. Carefully add water and partition between ethyl acetate and 5% hydrochloric acid. Separate the organic phase, wash with brine and dry (MgSO$_4$). Evaporate the solvent in vacuo and purify by silica gel chromatography to give 3,4-(dihydroxymethyl)furan.

Dissolve 3,4-(dihydroxymethyl)furan (11.9 g, 0.093 mol) in 2,4,6-collidine (12.4 g) and add a solution of lithium bromide (7.9 g, 91 mmol) in dimethylformamide (80 mL). Cool to −50° C. and place under a nitrogen atmosphere. Add methanesulfonyl chloride (11.8 g) at a rate which keeps the temperature under 0° C. Stir at 0° C. for 2 hours and pour onto ice water. Extract with ethyl ether, dry (MgSO$_4$), evaporate the solvent in vacuo and purify by silica gel chromatography to give 3,4-(dibromomethyl)furan.

Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add 3,4-(dibromomethyl)furan (23.8 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 5,5-(dicarboethoxy)-2,4,5,6-tetrahydro-cyclopenta[c]furan.

Dissolve 5,5-(dicarboethoxy)-2,4,5,6-tetrahydro-cyclopenta[c]furan (15.3 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry (Mg$_2$O$_4$) and pass through a silica gel plug to give 5-(carboethoxy)-2,4,5,6-tetrahydro-cyclopenta[c]furan.

Dissolve 5-(carboethoxy)-2,4,5,6-tetrahydro-cyclopenta[c]furan (6.2 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry (Na$_2$SO$_4$) and evaporate the solvent in vacuo to give 5-(carboxy)-2,4,5,6-tetrahydro-cyclopenta[c]furan.

Dissolve 5-(carboxy)-2,4,5,6-tetrahydro-cyclopenta[c]furan (3.6 g, 23.5 mmol) in methanol (60 mL) and treat with dimethoxypropane (5.8 mL, 47 mmol) and sulfuric acid (0.8 mL). Stir at room temperature for 1 day. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry (Na$_2$SO$_4$). Evaporate the solvent in vacuo and pass through a plug of silica gel to give 5-(carbomethoxy)-2,4,5,6-tetrahydro-cyclopenta[c]furan.

Mix 4-methoxybenzylthiol (3.0 g, 19 mmol) in sodium hydroxide (20 mL of a 2.5N aqueous solution) and methanol (10 mL). Add saturated aqueous copper sulfate solution (1.5 mL) and stir at room temperature for 2 hours, blowing air over the top of the mixture. Filter, wash solid with water and dry to give 4-methoxybenzyl disulfide as a pale yellow powder (2.71 g, 91%).

Cool lithium hexamethyldisilazane (4.2 mL, 4.2 mol, 1.0M in tetrahydrofuran) to −78° C. and treat with a solution of 5-(carbomethoxy)-2,4,5,6-tetrahydro-cyclopenta[c]furan (589 mg, 3.55 mmol) in tetrahydrofuran (5 mL). Stir for 1 hour then add hexamethylphosphoramide (0.93 mL, 5.3 mmol) and stir for 5 minutes. Add 4-methoxybenzyl disulfide (1.6 g, 5.2 mmol) in tetrahydrofuran (10 mL). Stir for 5 hours at −78° C. and quench with a solution of ammonium chloride. Partition between ethyl acetate (75 mL) and brine (30 mL). Dry (Na$_2$SO$_4$), evaporate the solvent in vacuo and purify by silica gel chromatography to give 5-(carbomethoxy)-5-(4-methoxybenzylthio)-2,4,5,6-tetrahydro-cyclopenta[c]furan.

Dissolve 5-(carbomethoxy)-5-(4-methoxybenzylthio)-2,4,5,6-tetrahydro-cyclopenta[c]furan (1.08 g, 3.55 mmol) in 95% ethanol (25 mL), water (12 mL) and tetrahydrofuran (15 mL). Treat with potassium hydroxide (1.3 g, 23 mmol) and stir at room temperature for 1 hour. Filter and evaporate the solvent in vacuo. Partition between water (125 mL) and ether (75 mL). Separate the aqueous phase and acidify with cold concentrated hydrochloric acid. Extract with methylene chloride (75 mL), dry (Na$_2$SO$_4$) and evaporate the solvent in vacuo. Purify by silica gel chromatography to give 5-(carboxy)-5-(4-methoxybenzylthio)-2,4,5,6-tetrahydro-cyclopenta[c]furan.

Dissolve [4α, 7α(R*), 12bβ]-7-(amino)-1,2,3,4,6,7,8,12b-octahydro-6-oxopyrido[2,1-a][2]benzazepine (136 mg, 0.59 mmol) and EDC (170 mg, 0.886 mmol) in tetrahydrofuran (5 mL). Treat with 5-(carboxy)-5-(4-methoxybenzylthio)-2,4,5,6-tetrahydro-cyclopenta[c]furan (0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry (Na$_2$SO$_4$) and evaporate the solvent in vacuo. Purify by silica gel chromatography to give the title compound.

Scheme A, step b: [4S-[4α, 7α(R*), 12bβ]]-7-[(5-Thio-5-oxo-4,5,6-trihydro-cyclopenta[c]furan)methylamino]-3,4,6,7,8,12b-hexahydro-6-oxo-1H-[1,4]-thiazino[3,4-a][2]benzazepine Dissolve [4S-[4α, 7α(R*), 12bβ]]-7-[(5-(4-methoxybenzylthio)-5-oxo-2,4,5,6-tetrahydro-cyclopenta[c]furan)methylamino]-3,4,6,7,8,12b-hexahydro- 6-oxo-1H-[1,4]-thiazino[3,4-a][2]benzazepine (0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry (Na$_2$SO$_4$) and evaporate the solvent in vacuo. Purify by silica gel chromatography to give the title compound.

EXAMPLE 8

Preparation of [4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2]benzazepine Scheme A, step a: [4S-[4α, 7α(R*), 12bβ]]-7-[(5-(4-methoxybenzylthio)-5-oxo-2,4,5,6-tetrahydro-cyclopenta[c]thiophene)methylamino]-3,4,6,7,8,12b-hexahydro-6-oxo-1H-[1,4]-thiazino[3,4-a][2]benzazepine Dissolve 3,4-(dicarboethoxy)thiophene (2.28 g, 10 mmol) in anhydrous tetrahydrofuran (30 mL) and cool to −20° C. Treat with lithium borohydride (7 mL of a 2N solution) and stir under a nitrogen atmosphere for several days. Carefully add water and partition between ethyl acetate and 5% hydrochloric acid. Separate the organic phase, wash with brine and dry (MgSO$_4$). Evaporate the solvent in vacuo and purify by silica gel chromatography to give 3,4-(dihydroxymethyl)thiophene.

Dissolve 3,4-(dihydroxymethyl)thiophene (13.4 g, 0.093 mol) in 2,4,6-collidine (12.4 g) and add a solution of lithium bromide (7.9 g, 91 mmol) in dimethylformamide (80 mL). Cool to −50° C. and place under a nitrogen atmosphere. Add trifluoromethanesulfonyl chloride (11.8 g) at a rate which keeps the temperature under 0° C. Stir at 0° C. for 2 hours and pour onto ice water. Extract with ethyl ether, dry (MgSO$_4$), evaporate the solvent in vacuo and purify by silica gel chromatography to give 3,4-(dibromomethyl)thiophene.

Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add 3,4-(dibromomethyl)thiophene (25.4 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 5,5-(dicarboethoxy)-2,4, 5,6-tetrahydro-cyclopenta[c]thiophene.

Dissolve 5,5-(dicarboethoxy)-2,4,5,6-tetrahydro-cyclopenta[c]thiophene (16.2 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry (MgSO$_4$) and pass through a silica gel plug to give 5-(carboethoxy)-2,4,5,6-tetrahydro-cyclopenta[c]thiophene.

Dissolve 5-(carboethoxy)-2,4,5,6-tetrahydro-cyclopenta [c]thiophene (6.68 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry (Na$_2$SO$_4$) and evaporate the solvent in vacuo to give 5-(carboxy)-2,4,5,6-tetrahydro-cyclopenta[c]thiophene.

Dissolve 5-(carboxy)-2,4,5,6-tetrahydro-cyclopenta[c]thiophene (3.95 g, 23.5 mmol) in methanol (60 mL) and treat with dimethoxypropane (5.8 mL, 47 mmol) and sulfuric acid (0.8 mL). Stir at room temperature for 1 day. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry (Na$_2$SO$_4$). Evaporate the solvent in vacuo and pass through a plug of silica gel to give 5-(carbomethoxy)-2,4,5,6-tetrahydro-cyclopenta[c]thiophene.

Mix 4-methoxybenzylthiol (3.0 g, 19 mmol) in sodium hydroxide (20 mL of a 2.5N aqueous solution) and methanol (10 mL). Add saturated aqueous copper sulfate solution (1.5 mL) and stir at room temperature for 2 hours, blowing air over the top of the mixture. Filter, wash solid with water and dry to give 4-methoxybenzyl disulfide as a pale yellow powder (2.71 g, 91%).

Cool lithium hexamethyldisilazane (4.2 mL, 4.2 mol, 1.0M in tetrahydrofuran) to −78° C. and treat with a solution of 5-(carbomethoxy)-2,4,5,6-tetrahydro-cyclopenta[c] thiophene (646 mg, 3.55 mmol) in tetrahydrofuran (5 mL). Stir for 1 hour then add hexamethylphosphoramide (0.93 mL, 5.3 mmol) and stir for 5 minutes. Add 4-methoxybenzyl disulfide (1.6 g, 5.2 mmol) in tetrahydrofuran (10 mL). Stir for 5 hours at −78° C. and quench with a solution of ammonium chloride. Partition between ethyl acetate (75 mL) and brine (30 mL). Dry (Na$_2$SO$_4$), evaporate the solvent in vacuo and purify by silica gel chromatography to give 5-(carbomethoxy)-5-(4-methoxybenzylthio)-2,4,5,6-tetrahydro-cyclopenta[c]thiophene.

Dissolve 5-(carbomethoxy)-5-(4-methoxybenzylthio)-2, 4,5,6-tetrahydro-cyclopenta[c]thiophene (1.14 g, 3.55 mmol) in 95% ethanol (25 mL), water (12 mL) and tetrahydrofuran (15 mL). Treat with potassium hydroxide (1.3 g, 23 mmol) and stir at room temperature for 1 hour. Filter and evaporate the solvent in vacuo. Partition between water (125 mL) and ether (75 mL). Separate the aqueous phase and acidify with cold concentrated hydrochloric acid. Extract with methylene chloride (75 mL), dry (Na$_2$SO$_4$) and evaporate the solvent in vacuo. Purify by silica gel chromatography to give 5-(carboxy)-5-(4-methoxybenzylthio)-2,4,5,6-tetrahydro-cyclopenta[c]thiophene.

Dissolve [4α, 7α(R*), 12bβ]-7-(amino)-1,2,3,4,6,7,8, 12b-octahydro-6-oxopyrido[2,1-a][2]benzazepine (136 mg, 0.59 mmol) and EDC (170 mg, 0.886 mmol) in tetrahydrofuran (5 mL). Treat with 5-(carboxy)-5-(4-methoxybenzylthio)-2,4,5,6-tetrahydro-cyclopenta[c]thiophene (0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry (Na$_2$SO$_4$) and evaporate the solvent in vacuo. Purify by silica gel chromatography to give the title compound.

Scheme A, step b: [[4S-[4α, 7α(R*), 12bβ]]-7-[(5-Thio-5-oxo-4,5,6-trihydro-cyclopenta[c]thiophene)methylamino]-3,4,6,7,8,12b-hexahydro-6-oxo-1H-[1,4]-thiazino[3,4-a][2] benzazepine Dissolve [[4S-[4α, 7α(R*), 12bβ]]-7-[(5-(4-methoxybenzylthio)-5-oxo-2,4,5,6-tetrahydro-cyclopenta [c]thiophene)methylamino]-3,4,6,7,8,12b-hexahydro-6-oxo-1H-[1,4]-thiazino[3,4-a][2]benzazepine (0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry (Na$_2$SO$_4$) and evaporate the solvent in vacuo. Purify by silica gel chromatography to give the title compound.

EXAMPLE 9

Preparation of [4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4]-azazino[3,4-a][2] benzazepine Scheme C, step a: [(R*,R*)]-N-[2-(1,3-Dihydro-1,3-dioxo-2H-isoindol- 2-yl)-1-oxo-3-phenylpropyl]-3,4-dihydro-2H-4-trifluoroacetyl-1,4-azazine Dissolve ethylenediamine (30 mL, 0.45 mol) in dioxane (150 ml). Add, by dropwise addition over 2.5 hours, a solution of di-tert-butyldicarbonate (12.2 g, 56.1 mmol) in anhydrous dioxane (150 mL). Stir at room temperature for 22 hours, evaporate the solvent in vacuo and add water (250 mL). Filter and extract the aqueous phase with methylene chloride (3×250 mL). Dry (Na$_2$SO$_4$) and evaporate the solvent in vacuo to give N-(t-butyloxycarbonyl)ethylenediamine as a colorless oil (8.82 g, 25 98%).

Dissolve N-(t-butyloxycarbonyl)ethylenediamine (8.82 g, 55.1 mmol) in methylene chloride (150 mL). Treat with pyridine (6.7 mL, 83 mmol). Add, by dropwise addition, trifluoroacetic anhydride (11.7 mL, 83 mmol). Stir at room temperature for 2.5 hours and quench with saturated sodium hydrogen carbonate (50 mL). Extract and wash the organic phase with 5% sulfuric acid (50 mL) and again with saturated sodium hydrogen carbonate (50 mL). Dry (Na$_2$SO$_4$), evaporate the solvent in vacuo and purify by chromatography (2:1 ethyl acetate/hexane) to give N-(t-butyloxycarbonyl)-N'-(trifluoroacetyl)-ethylenediamine as a colorless oil (10.1 g, 72%).

Dissolve N-(t-butyloxycarbonyl)-N'-(trifluoroacetyl)-ethylenediamine (500 mg, 1.95 mmol) in anhydrous dimethylformamide (10 mL), cool to 0° C. and treat with sodium hydride (56 mg, 1.85 mmol, 80% dispersion in mineral oil). Stir for 15 minutes and add allyl bromide (0.25 mL, 2.9 mmol). Stir for 2.5 hours, dilute with ethyl acetate (50 mL) and extract with water (25 mL). Separate the organic phase and wash with brine (2×20 mL). Extract the combined aqueous phases with ethyl acetate (2×5 mL), dry ($Na_2SO_4$) and evaporate the solvent in vacuo. Purify by chromatography (2:1 hexane/ethyl acetate to 3:2 hexane/ethyl acetate) to give N-(t-butyloxycarbonyl)-N'-(trifluoroacetyl)-N'-(allyl)-ethylenediamine (562 mg, 100%).

Dissolve N-(t-butyloxycarbonyl)-N'-(trifluoroacetyl)-N'-(allyl)-ethylenediamine (1.95 mmol) in methylene chloride (7 mL) and add trifluoroacetic acid (2.6 mL). Stir at room temperature for 1 hour then evaporate the solvent in vacuo to give N'-(trifluoroacetyl)-N'-(allyl)-ethylenediamine trifluoroacetate.

Suspend N'-(trifluoroacetyl)-N'-(allyl)-ethylenediamine trifluoroacetate (1.95 mmol) in methylene chloride (7 mL) and add N-phthaloyl-(S)-phenylalanine, acid chloride (3 mL, 2.5 mmol). Cool to −30° C. and add, by dropwise addition, N-methylmorpholine (0.46 mL, 4.2 mmol). Stir for 2 hours and dilute with ethyl acetate (50 mL). Wash with 5% sulfuric acid (20 mL), saturated sodium hydrogen carbonate (20 mL) and brine (20 mL). Dry ($Na_2SO_4$), evaporate the solvent in vacuo and purify by chromatography (2:1 hexane/ethyl acetate) to give N-[2-(1,3-dihydro-1,3-dioxo-2H-isoindol-2-yl)-1-oxo- 3-phenylpropyl]-N'-(trifluoroacetyl)-N'-(allyl)-ethylenediamine (540 mg, 58%).

Dissolve N-[2-(1,3-dihydro-1,3-dioxo-2H-isoindol-2-yl)-1-oxo-3-phenylpropyl]-N'-(trifluoroacetyl)-N'-(allyl)-ethylenediamine (600 mg, 1.27 mmol) in methylene chloride (22 mL) and methanol (22 mL). Cool to −78° C. and treat with ozone until blue. Remove excess ozone with a stream of nitrogen and add pyridine (0.12 mL) followed by dimethylsulfide (2.5 mL) and warm gradually to room temperature overnight. Dilute with ethyl acetate (75 mL) and wash with 5% sulfuric acid (30 mL) and saturated sodium hydrogen carbonate (30 mL). Dry ($Na_2SO_4$), evaporate the solvent in vacuo and purify by chromatography (2.5:1 ethyl acetate/hexane) to give 2-(1,3-dihydro-1,3-dioxo-2H-isoindol-2-yl)-1-oxo-3-phenylpropyl-N'-(trifluoroacetyl)-N,-(1-oxo-ethane)-ethylenediamine as a white foam (489 mg, 81%).

Dissolve 2-(1,3-dihydro-1,3-dioxo-2H-isoindol-2-yl)-1-oxo-3-phenylpropyl-N'-(trifluoroacetyl)-N'-(1-oxo-ethane)-ethylenediamine (200 mg, 0.41 mmol) in methylene chloride (8 mL) and treat with trifluoroacetic acid (0.5 mL, 0.65 mmol). Stir for 2 hours at room temperature and dilute with ethyl acetate (50 mL). Wash with saturated sodium hydrogen carbonate (20 mL), then brine (20 mL) and dry ($Na_2SO_4$). Evaporate the solvent in vacuo and purify by chromatography (2:1 hexane/ethyl acetate) to give the title compound (90 mg, 47%).

Scheme C, step b: [4α, 7α(R*), 12bβ]-7-[(1,3-Dihydro-1,3-dioxo-2H-isoindol-2-yl)]-3,4,6,7,8,12b-hexahydro-6-oxo-1H-4-trifluoroacetyl-[1,4]-azazino[3,4-a][2]benzazepine Dissolve [(R*,R*)]-N-[2-(1,3-dihydro-1,3-dioxo-2H-isoindol- 2-yl)-1-oxo-3-phenylpropyl]-3,4-dihydro-2H-4-trifluoroacetyl-1,4-azazine (1.73 mmol) in methylene chloride (14 mL) and add, by dropwise addition, to trifluoromethane sulfonic acid (7 mL). Stir at room temperature for 4.5 days, cool in an ice bath and quench with water (3 mL). Partition between ethyl acetate (100 mL) and water (30 mL). Separate the organic phase and wash with saturated sodium hydrogen carbonate (30 mL), dry ($Na_2SO_4$), evaporate the solvent in vacuo and purify by chromatography to give the title compound.

Scheme C, step c: [4α, 7α(R*), 12bβ]-7-(Amino)-3,4,6,7,8,12b-hexahydro-6-oxo-1H-4-t-butyloxycarbonyl-[1,4]-azazino[3,4-a][2]benzazepine Dissolve [4α, 7α(R*), 12bβ]-7-[(1,3-dihydro-1,3-dioxo-2H-isoindol-2-yl)]-3,4,6,7,8,12b-hexahydro-6-oxo-1H-4-trifluoroacetyl-[1,4]-azazino[3,4-a][2]benzazepine (9 mmol) in anhydrous tetrahydrofuran (30 mL) and treat with pyrrolidine (10 mmol). Stir at room temperature for 48 hours and evaporate the solvent in vacuo to give [4α, 7α(R*), 12bβ] -7-[o-pyrrolidinocarbonylbenzamide]-3,4,6,7,8,12b-hexahydro-6-oxo-1H-4-trifluoroacetyl-[1,4]-azazino[3,4-a][2]benzazepine.

Dissolve [4α, 7α(R*), 12bβ]-7-[o-pyrrolidinocarbonylbenzamide ]-3,4,6,7,8,12b-hexahydro-6-oxo-1H-4-trifluoroacetyl-[1,4]-azazino[3,4-a][2]benzazepine (1.5 mmol) in a mixture of ethanol (3 mL) and acetone (3 mL). Add sodium borohydride (1.5 mmol) and stir at room temperature overnight. Pour into water (25 mL) and carefully neutralize with 1N hydrochloric acid. Extract into ethyl acetate (2×), dry ($MgSO_4$) and evaporate the solvent in vacuo to give [4α, 7α(R*), 12bβ]-7-[o-pyrrolidinocarbonylbenzamide]-3,4,6, 7,8,12b-hexahydro-6-oxo-1H-[1,4]-azazino[3,4-a][2]benzazepine.

Dissolve [4α, 7α(R*), 12bβ]-7-[o-pyrrolidinocarbonylbenzamide]-3,4,6,7,8,12b-hexahydro-6-oxo-1H-[1,4]-azazino[3,4-a][2]benzazepine (1 mmol) in methanolic hydrochloric acid (5 mL) and stir at room temperature overnight. Evaporate the solvent in vacuo to give [4α, 7α(R*), 12bβ] -7-[(1,3-dihydro-1,3-dioxo-2H-isoindol-2-yl)]-3,4,6,7,8, 12b-hexahydro-6-oxo-1H-[1,4]-azazino[3,4-a][2]benzazepine.

Dissolve [4α, 7α(R*), 12bβ]-7-[(1,3-dihydro-1,3-dioxo-2H-isoindol-2-yl)]-3,4,6,7,8,12b-hexahydro-6-oxo-1H-[1,4]-azazino[3,4-a][2]benzazepine (5 mmol) in 50/50 dioxane/water (25 mL) and buffer to pH 10 with 1N sodium hydroxide. Add, by dropwise addition, an ether solution of di-t-butyl dicarbonate (1.2 g, 5.5 mmol) at 10° C. Allow to warm to room temperature and buffer occasionally to retain pH 10. Acidify with a sodium citrate/citric acid buffer to pH 5, extract with ether (3×), dry ($MgSO_4$) and evaporate the solvent in vacuo to give [4α, 7α(R*), 12bβ]-7-[(1,3-dihydro-1,3-dioxo-2H-isoindol-2-yl)]-3,4,6,7,8,12b-hexahydro-6-oxo-1H-4-t-butyloxycarbonyl-[1,4]-azazino[3,4-a][2]benzazepine.

Dissolve [4α, 7α(R*), 12bβ]-7-[(1,3-dihydro-1,3-dioxo-2H-isoindol-2-yl)]-3,4,6,7,8,12b-hexahydro-6-oxo-1H-4-t-butyloxycarbonyl-[1,4]-azazino[3,4-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and $MgSO_4$ and evaporate the solvent in in vacuo to give the title compound.

Scheme A, step a: [4S-[4α, 7α(R*), 12bβ]]-7-[(5-(4-methoxybenzylthio)-5-oxo-2-(carbo-t-butyloxy)-2,4,5,6-tetrahydro-cyclopenta[c]pyrrole)methylamino]-3,4,6,7,8,12b-hexahydro-6-oxo-1H-4-t-butyloxycarbonyl-[1,4]-azazino[3, 4-a][2]benzazepine Dissolve 3,4-(dicarboethoxy)pyrrole (1.06 g, 5 mmol) in 50/50 dioxane water (25 mL) and buffer to pH 10 with 1N sodium hydroxide. Add, by dropwise addition, an ether solution of di-t-butyl dicarbonate (1.2 g, 5.5 mmol) at 10° C. Allow to warm to room temperature and buffer occasionally to retain pH 10. Acidify with a sodium citrate/citric acid buffer to pH 5, extract with ethyl ether (3×), dry ($MgSO_4$)

and evaporate the solvent in vacuo. Purify the residue by silica gel chromatography to give N-(carbo-t-butyloxy)-3,4-(dicarboethoxy)pyrrole.

Dissolve N-(carbo-t-butyloxy)-3,4-(dicarboethoxy)pyrrole (3.11 g, 10 mmol) in anhydrous tetrahydrofuran (30 mL) and cool to −20° C. Treat with lithium borohydride (7 mL of a 2N solution) and stir under a nitrogen atmosphere for several days. Carefully add water and partition between ethyl acetate and 5% hydrochloric acid. Separate the organic phase, wash with brine and dry ($MgSO_4$). Evaporate the solvent in vacuo and purify by silica gel chromatography to give N-(carbo-t-butyloxy)-3,4-(dihydroxymethyl)pyrrole.

Dissolve N-bromosuccinimide (1.78 g, 0.01 mol) in tetrahydrofuran (60 mL) and add a solution of triphenylphosphine (2.62 g, 0.01 mol) in tetrahydrofuran. Add a solution of N-(carbo-t-butyloxy)-3,4-(dihydroxymethyl)pyrrole (1.14 g, 5 mmol) in tetrahydrofuran (25 mL) and stir until most of the solid goes into solution. Evaporate the solvent in vacuo and partition the residue between water and ethyl ether. Separate the organic phase and wash with water. Dry ($Na_2SO_4$) and evaporate the solvent in vacuo. Purify by silica gel chromatography to give N-(carbo-t-butyloxy)-3,4-(dibromomethyl)pyrrole.

Dissolve diethylmalonate (15.2 mL, 0.100 mol) in tetrahydrofuran (800 mL). Cool in an ice bath and treat with sodium hydride (3.0 g, 0.10 mol, 80% in mineral oil). Stir until solution attained and add N-(carbo-t-butyloxy)-3,4-(dibromomethyl)pyrrole (35.3 g, 0.100 mol). Stir for 30 minutes then add additional sodium hydride (3.0 g, 0.10 mol). Stir at room temperature for 20 hours, filter through filter aid and evaporate the solvent in vacuo. Purify by silica gel chromatography to give 5,5-(dicarboethoxy)-2-(carbo-t-butyloxy)-2,4,5,6-tetrahydro-cyclopenta[c]pyrrole.

Dissolve 5,5-(dicarboethoxy)-2-(carbo-t-butyloxy)-2,4,5,6-tetrahydro-cyclopenta[c]pyrrole (21.3 g, 60.6 mmol) in dimethylsulfoxide (140 ml). Add water (14 mL) and lithium chloride (7.0 g, 0.16 mol). Heat at reflux for 4 hours, cool and partition between water (150 mL) and methylene chloride (2×150 mL). Wash the organic phase with water (150 mL), dry ($MgSO_4$) and pass through a silica gel plug to give 5-(carboethoxy)-2-(carbo-t-butyloxy)-2,4,5,6-tetrahydro-cyclopenta[c]pyrrole.

Dissolve 5-(carboethoxy)-2-(carbo-t-butyloxy)-2,4,5,6-tetrahydro-cyclopenta[c]pyrrole (9.5 g, 34.1 mmol) in ethanol (95%, 150 mL) and water (75 mL). Add potassium hydroxide (9.5 g, 0.17 mol) and stir at room temperature for 1 hour. Partition between water (150 mL) and ethyl ether (2×150 mL). Acidify the aqueous phase with hydrochloric acid to pH 1. Extract with methylene chloride (2×150 mL), dry ($Na_2SO_4$) and evaporate the solvent in vacuo to give 5-(carboxy)-2-(carbo-t-butyloxy)-2,4,5,6-tetrahydro-cyclopenta[c]pyrrole.

Dissolve 5-(carboxy)-2-(carbo-t-butyloxy)-2,4,5,6-tetrahydro-cyclopenta[c]pyrrole (5.9 g, 23.5 mmol) in methanol (60 mL) and treat with dimethoxypropane (5.8 mL, 47 mmol) and sulfuric acid (0.8 mL). Stir at room temperature for 1 day. Evaporate the solvent in vacuo, dilute with methylene chloride (75 mL) and wash with saturated sodium hydrogen carbonate (35 mL). Extract the aqueous phase with methylene chloride (30 mL), wash combined organics with brine (30 mL) and dry ($Na_2SO_4$). Evaporate the solvent in vacuo and pass through a plug of silica gel to give 5-(carbomethoxy)-2-(carbo-t-butyloxy)-2,4,5,6-tetrahydro-cyclopenta[c]pyrrole.

Mix 4-methoxybenzylthiol (3.0 g, 19 mmol) in sodium hydroxide (20 mL of a 2.5N aqueous solution) and methanol (10 mL). Add saturated aqueous copper sulfate solution (1.5 mL) and stir at room temperature for 2 hours, blowing air over the top of the mixture. Filter, wash solid with water and dry to give 4-methoxybenzyl disulfide as a pale yellow powder (2.71 g, 91%).

Cool lithium hexamethyldisilazane (4.2 mL, 4.2 mol, 1.0M in tetrahydrofuran) to −78° C. and treat with a solution of 5-(carbomethoxy)-2-(carbo-t-butyloxy)-2,4,5,6-tetrahydro-cyclopenta[c]pyrrole (941 mg, 3.55 mmol) in tetrahydrofuran (5 mL). Stir for 1 hour then add hexamethylphosphoramide (0.93 mL, 5.3 mmol) and stir for 5 minutes. Add 4-methoxybenzyl disulfide (1.6 g, 5.2 mmol) in tetrahydrofuran (10 mL). Stir for 5 hours at −78° C. and quench with a solution of ammonium chloride. Partition between ethyl acetate (75 mL) and brine (30 mL). Dry ($Na_2SO_4$), evaporate the solvent in vacuo and purify by silica gel chromatography to give 5-(carbomethoxy)-2-(carbo-t-butyloxy)-5-(4-methoxybenzylthio)-2,4,5,6-tetrahydro-cyclopenta[c]pyrrole.

Dissolve 5-(carbomethoxy)-2-(carbo-t-butyloxy)-5-(4-methoxybenzylthio)-2,4,5,6-tetrahydro-cyclopenta[c]pyrrole (1.43 g, 3.55 mmol) in 95% ethanol (25 mL), water (12 mL) and tetrahydrofuran (15 mL). Treat with potassium hydroxide (1.3 g, 23 mmol) and stir at room temperature for 1 hour. Filter and evaporate the solvent in vacuo. Partition between water (125 mL) and ether (75 mL). Separate the aqueous phase and acidify with cold concentrated hydrochloric acid. Extract with methylene chloride (75 mL), dry ($Na_2SO_4$) and evaporate the solvent in vacuo. Purify by silica gel chromatography to give 5-(carboxy)-2-(carbo-t-butyloxy)- 5-(4-methoxybenzylthio)-2,4,5,6-tetrahydro-cyclopenta[c]pyrrole.

Dissolve [4α, 7α(R*), 12bβ]-7-(amino)-3,4,6,7,8,12b-hexahydro- 6-oxo-1H-4-t-butyloxycarbonyl-[1,4]-azazino[3,4-a][2]benzazepine (136 mg, 0.59 mmol) and EDC (170 mg, 0.886 mmol) in tetrahydrofuran (5 mL). Treat with 5-(carboxy)-2-(carbo-t-butyloxy)- 5-(4-methoxybenzylthio)-2,4,5,6-tetrahydro-cyclopenta[c]pyrrole (0.74 mmol). Stir at room temperature under an argon atmosphere for 20 hours and evaporate the solvent in vacuo. Dissolve the residue in ethyl acetate (30 mL) and wash with 5% sulfuric acid (15 ml) then saturated sodium hydrogen carbonate (15 mL). Dry ($Na_2SO_4$) and evaporate the solvent in vacuo. Purify by silica gel chromatography to give the title compound.

Scheme a, step b: [4S-[4α, 7α(R*), 12bβ]]-7-[(5-Thio-5-oxo-2,4,5,6-tetrahydro-cyclopenta[c]pyrrole)methylamino]-3,4,6,7,8,12b-hexahydro-6-oxo-1H-[1,4]-azazino[3,4-a][2]benzazepine Dissolve [4S-[4α, 7α(R*), 12bβ]]-7-[(5-(4-methoxybenzylthio)-5-oxo-2-(carbo-t-butyloxy)-2,4,5,6-tetrahydro-cyclopenta[c]pyrrole)methylamino]-3,4,6,7,8,12b-hexahydro-6-oxo-1H-4-t-butyloxycarbonyl-[1,4]-azazino[3,4-a][2]benzazepine (0.38 mmol) in methylene chloride (6 mL) and cool to 0° C. Treat with trifluoroacetic acid (3 mL), anisole (0.42 mL, 3.8 mmol), and mercuric acetate (155 mg, 0.49 mmol). Stir at 0° C. for 3 hours then bubble hydrogen sulfide gas through the solution for 15 minutes. Filter and wash with methylene chloride. Wash organic phase with water (20 mL), dry ($Na_2SO_4$) and evaporate the solvent in vacuo. Purify by silica gel chromatography to give the title compound.

EXAMPLE 10

[6α(R*), 11bβ]-6-[(S)-(5-Thio-5-oxo-2,4,5,6-tetrahydro-cyclopenta[c]pyrrole)methylamino]-1,2,3,5,6,7,11b-heptahydro-5-oxo-pyrrolo[2,1-a][2]benzazepine Scheme C, step a: (R*,R*)-N-[2-(1,3-Dihydro-1,3-dioxo-2H-isoindol-2-yl)-1-oxo-3-phenylpropyl]-1,2,3-trihydro-2- pyrrole

Mix 4-bromo-1-butene (0.209 mol) and potassium cyanide (16.8 g, 0.257 mol) in ethylene glycol (85 mL) and heat at 100° C. for 2 hours. Cool, dilute with water (100 mL) and extract into ethyl ether (100 mL). Wash with saturated sodium hydrogen carbonate (35 mL), dry ($Na_2SO_4$) and distill to give 4-pentenylnitrile.

Suspend lithium aluminum hydride (6.5 g, 0.17 mol) in ethyl ether (350 mL) and add, by dropwise addition over 30 minutes, 4-pentenylnitrile (0.171 mol). Stir at room temperature for 2 hours, cool in an ice bath and add, by very slow addition, water (6.8 mL), then 20% sodium hydroxide (5.2 mL) then water (24 mL). Decant the ethereal phase and wash the white salts with ether. Combine the ethereal phases and distill to give 4-penteneamine.

Dissolve 4-pentenylamine (0.88 g, 8.9 mmol) in methylene chloride (50 mL) and treat first with N-phthaloyl-(S)-phenylalanine (2.95 g, 10.0 mmol), then with EEDQ (2.47 g, 10.0 mmol) and stir at room temperature for 6 hours. Evaporate the solvent in vacuo, dissolve the residue in ethyl acetate (75 mL) and wash with 5% sulfuric acid (25 mL), saturated sodium hydrogen carbonate (25 mL) and brine (25 mL). Dry ($Na_2SO_4$), evaporate the solvent in vacuo and purify by chromatography to give 2-(1,3-dihydro-1,3-dioxo-2H-isoindol-2-yl)-3-phenylpropionyl-4-pentenylamide.

Dissolve 2-(1,3-dihydro-1,3-dioxo-2H-isoindol-2-yl)-3-phenylpropionyl-4-pentenylamide (3.19 mmol) in methylene chloride (40 mL) and methanol (4 mL), cool to −78° C. and place under a nitrogen atmosphere. Treat with ozone until a blue color persists, degas with nitrogen for 20 minutes and add pyridine (0.2 mL). Quench with dimethylsulfide (4 mL) and stir overnight at room temperature. Dilute with methylene chloride (75 mL) and wash with 5% sulfuric acid (40 mL) and brine (40 mL). Dry ($Na_2SO_4$), evaporate the solvent in vacuo and purify by chromatography (hexane/ethyl acetate) to give 2-(1,3-dihydro-1,3-dioxo-2H-isoindol-2-yl)-3-phenylpropionyl-4-oxo-butylamide.

Dissolve 2-(1,3-dihydro-1,3-dioxo-2H-isoindol-2-yl)-3-phenylpropionyl-4-oxo-butylamide (0.404 mmol) in anhydrous methylene chloride (7 mL) and treat with trifluoroacetic acid (0.04 mL, 0.5 mmol). Stir at room temperature for 3 hours, partition between methylene chloride (25 mL) and saturated sodium hydrogen carbonate (15 mL). Dry ($Na_2SO_4$), evaporate the solvent in vacuo and purify by chromatography to give the title compound.

Scheme C, step b: [6α(R*), 11bβ]-6-[(S)-(1,3-Dihydro-1,3-dioxo-2H-isoindol-2-yl)]-3,5,6,7,11b-heptahydro-5-oxo-pyrrolo[2,1-a][2]benzazepine Dissolve (R*,R*)-N-[2-(1,3-dihydro-1,3-dioxo-2H-isoindol-2-yl)-1-oxo-3-phenylpropyl]-1,2,3-trihydro-2-pyrrole (1.73 mmol) in methylene chloride (14 mL) and add, by dropwise addition, to trifluoromethane sulfonic acid (7 mL). Stir at room temperature for 4.5 hours, cool in an ice bath and quench with water (3 mL). Partition between ethyl acetate (100 mL) and water (30 mL). Separate the organic phase and wash with saturated sodium hydrogen carbonate (30 mL), dry ($Na_2SO_4$), evaporate the solvent in vacuo and purify by chromatography to give the title compound.

Scheme C, step c: [6α(R*), 11bβ]-6-[(S)-Amino]-3,5,6,7,11b-heptahydro-5-oxo-pyrrolo[2,1-a][2]benzazepine Dissolve [6α(R*), 11bβ]-6-[(S)-(1,3-dihydro-1,3-dioxo-2H-isoindol-2-yl)]-3,5,6,7,11b-heptahydro-5-oxo-pyrrolo[2,1-a][2]benzazepine (1.86 mmol) in methanol (15 mL) and treat with hydrazine hydrate (4.6 mL of a 1.0M solution in methanol, 4.6 mmol). Stir 2.5 days at room temperature, filter through filter aid and condense. Filter again through a mixture of filter aid and MgSO4 and evaporate the solvent in vacuo to give the title compound.

Scheme A, step a: [6α(R*), 11bβ]-6-[(S)-(5-(4-Methoxybenzylthio)-5-oxo-2-(carbo-t-butyloxy)-2,4,5,6-tetrahydro-cyclopenta[c]pyrrole)methylamino]1,2,3,5,6,7,11b-heptahydro-5-oxo-pyrrolo[2,1-a][2]benzazepine Dissolve 5-(carboxy)-2-(carbo-t-butyloxy)-5-(4-methoxybenzylthio)-2,4,5,6-tetrahydro-cyclopenta[c]pyrrole (329 mg, 0.845 mmol) in methylene chloride (6 mL), cool in an ice-methanol bath and treat with oxalyl chloride (0.94 mL, 11 mmol). Stir for 1.5 hours, evaporate the solvent in vacuo at 0°–5° C. Dilute the residue with methylene chloride (3 mL) and add a solution of [6α(R*), 11bβ]-6-[(S)-Amino]-1,2,3,5,6,7,11b-heptahydro-5-oxo-pyrrolo[2,1-a][2]benzazepine (0.565 mmol) in methylene chloride (6 mL). Add pyridine (68 μL, 0.85 mmol) and stir for 2 hours. Dilute with ethyl acetate (60 mL) and wash with 1N hydrochloric acid (30 mL) and saturated sodium hydrogen carbonate (2×30 mL). Dry ($MgSO_4$), evaporate the solvent in vacuo and purify by silica gel chromatography to give the title compound.

Scheme A, step b: [6α(R*), 11bβ]-6-[(S)-(5-Thio-5-oxo-2,4,5,6-tetrahydro-cyclopenta[c]pyrrole)methylamino]-1,2,3,5,6,7,11b-heptahydro-5-oxo-pyrrolo[2-a][2]benzazepine Dissolve [6α(R*), 11bβ]-6-[(S)-(5-(4-methoxybenzylthio)-5-oxo-2-(carbo-t-butyloxy)-2,4,5,6-tetrahydro-cyclopenta[c]pyrrole)methylamino]-1,2,3,5,6,7,11b-heptahydro-5-oxo-pyrrolo[2,1-a][2]benzazepine (105 mg, 0.163 mmol) in methylene chloride (3 mL) and cool to 0° C. Treat with trifluoroacetic acid (1.5 mL), anisole (0.19 mL, 1.7 mmol), and mercuric acetate (65 mg, 0.2 mmol). Stir at 0° C. for 3 hours then bubble hydrogen sulfide gas through the solution for 10 minutes. Filter and wash with methylene chloride. Wash organic phase with water (20 mL), dry ($Na_2SO_4$) and evaporate the solvent in vacuo. Purify by silica gel chromatography to give the title compound.

EXAMPLE 11

[4S-[4α, 7α(R*), 12bβ]]-7-[(2-Thio-1-oxo-2-methyl)-2-propylamino]-1,2,3,4,6,7,8,12b-octahydro-6-oxopyrido[2,1-a][2]benzazepine Dissolve 4-methoxybenzylthiol (14 mL, 0.10 mmol) in anhydrous dimethylformamide (150 mL), degas and purge with nitrogen. Add diisopropylethylamine (20 ml, 0.115 mol), then treat with ethyl bromoacetate (11.1 mL, 0.10 mol). Place the reaction flask in a cooling bath containing cold water and stir to room temperature for 64 hours. Partition between water (300 mL) and ether (250 mL). Separate the aqueous phase and extract with ether (250 mL). Combine the organic phases, wash with water (2×150 mL) and extract the combined aqueous phases with ether (125 mL). Dry ($Na_2SO_4$) and evaporate the solvent in vacuo. Purify by chromatography (6:1 hexane/ethyl acetate) to give 1-(carboethoxy)-1-(4-methoxybenzylthio)methane as a yellow oil (22 g, 92%).

Dissolve lithium hexamethyldisilazane (4.2 mL of a 1.0M solution in tetrahydrofuran, 4.2 mmol) in tetrahydrofuran (9 mL) and cool to −78° C. Treat with a solution of 1-(carboethoxy)-1-(4-methoxybenzylthio)methane (1.0 g, 4.2 mmol) in tetrahydrofuran (4 mL). Stir for 45 minutes, add methyliodide (0.26 mL, 4.2 mmol) and stir for 3 hours. Add additional lithium hexamethyldisilazane (4.2 mL of a 1.0M solution in tetrahydrofuran, 4.2 mmol), stir for 30 minutes and add methyl iodide (0.3 mL, 4.8 mmol). Stir at room temperature overnight. Partition between saturated ammonium chloride (30 mL) and ethyl acetate (50 mL). Separate the organic phase, dry (Na$_2$SO$_4$) and evaporate the solvent in vacuo. Purify by chromatography (5:1 hexane/ethyl acetate) to give 2-(carboethoxy)-2-(4-methoxybenzylthio)propane as a pale yellow oil (1.05 g, 93.8%).

Dissolve 2-(carboethoxy)-2-(4-methoxybenzylthio)propane (1.05 g, 3.91 mmol) in a mixture of 95% ethanol (18 mL), water (9 mL) and tetrahydrofuran (10 mL). Add potassium hydroxide (1.4 g, 25 mmol) and stir at room temperature for 2 hours then at 55° C. for hour. Evaporate the solvent in vacuo and partition between water (50 mL) and ether (50 mL). Acidify to pH 1 with concentrated hydrochloric acid and extract into methylene chloride (50 mL). Dry (Na$_2$SO$_4$) and evaporate the solvent in vacuo to give 2-(carboxy)-2-(4-methoxybenzylthio)propane as a tan solid (763 mg).

Dissolve [4S-[4α, 7α(R*), 12bβ]]-7-(amino)-1,2,3,4,6,7,8,12b-octahydro-6-oxopyrido[2,1-a][2]benzazepine (175 mg) EEDQ (101 mg, 0.41 mmol) and 2-(carboxy)-2-(4-methoxybenzylthio)propane (96 mg, 0.40 mmol in methylene chloride (5 mL). Stir at room temperature for 18 hours and evaporate the solvent in vacuo. Dissolve the residue in ethyl acetate (30 mL) and wash with 5% sulfuric acid (15 ml) then saturated sodium hydrogen carbonate (15 mL). Dry (Na$_2$SO$_4$) and evaporate the solvent in vacuo. Purify by silica gel chromatography to give [4S-[4α, 7α(R*), 12bβ]]-7-[(2-(4-methoxybenzylthio)-1-oxo-2-methyl)-2-propylamino]-1,2,3,4,6,7,8,12b-octahydro-6-oxopyrido[2,1-a][2]benzazepine.

Dissolve [4S-[4α, 7α(R*), 12bβ]]-7-[(2-(4-methoxybenzylthio)-1-oxo-2-methyl)-2-propylamino]-1,2,3,4,6,7,8,12b-octahydro-6-oxopyrido[2,1-a][2]benzazepine (260 mg) in methylene chloride (5 mL) and cool to 0° C. Treat with anisole (0.43 mL, 4.0 mmol) and mercuric acetate (159 mg, 0.50 mmol) then with trifluoroacetic acid (2.5 mL). Stir for 3 hours then bubble hydrogen sulfide gas through the solution for 10 minutes. Filter and dilute with methylene chloride. Wash organic phase with water (20 mL), dry (Na$_2$SO$_4$) and evaporate the solvent in vacuo. Purify by silica gel chromatography to give the title compound. In a further embodiment, the present invention provides a method of inhibiting enkephalinase in a patient in need thereof comprising administering to said patient an effective enkephalinase inhibitory amount of a compound of Formula (I).

EXAMPLE 12

[4S-[4α, 7α(R*), 12bβ]]-7-[(4-Thio-4-oxopiperidine)methylamino]-1,2,3,4,6,7,8,12b-octahydro-6-oxopyrido[2,1-a][2]benzazepine Scheme A, step a: [4S-[4α, 7α(R*), 12bβ]]-7-[(4-(4-Methoxybenzylthio)-4-oxo-1-(carbo-t-butyloxy)-piperidine)methylamino]-1,2,3,4,6,7,8,12b-octahydro-6-oxopyrido[2,1-a][2]benzazepine Dissolve t-butyldicarbonate (14.14 g, 64.8 mmol) in methylene chloride (600 mL) and add ethyl isonipecotic acid (10 mL, 64.8 mmol). Stir for 1 hour and evaporate the solvent in vacuo to give 1-carbo-t-butyloxy-isonipecotic acid, ethyl ester as a pale yellow oil (17.5 g, 99%).

Add, by dropwise addition, 1-carbo-t-butyloxy-isonipecotic acid, ethyl ester (4 g, 15.546 mmol) to a solution of lithium diisopropylamide (27.96 mmol) in tetrahydrofuran at −78° C. Warm to −25° C. and add a solution of 4-methoxybenzyl disulfide (8.56 g, 27.96 mmol) in tetrahydrofuran (15 mL). Stir at room temperature for 1 hour, dilute with ethyl acetate (200 mL), wash with 10% HCl (2×100 mL) and saturated sodium hydrogen carbonate (100 mL). Dry (Na$_2$SO$_4$) and evaporate the solvent in vacuo. Purify by silica gel chromatography (1:9 ethyl acetate/hexane) to give (4-(carboethoxy)-4-(4-methoxybenzylthio)-1-(carbo-t-butyloxy)-piperidine.

Dissolve (4-(carboethoxy)-4-(4-methoxybenzylthio)-1-(carbo-t-butyloxy)-piperidine (3 g, 7.5 mmol) in a mixture of methanol, (35 mL) tetrahydrofuran (35 mL) and water (17 mL). Add lithium hydroxide monohydrate (2.2 g, 0.053 mol) and heat at 45°–60° C. for 5 hours. Cool, evaporate the solvent in vacuo and partition the residue between water (200 mL) and ether (200 mL). Separate the aqueous phase, acidify to pH 1 and extract with methylene chloride (200 mL). Dry (Na$_2$SO$_4$), evaporate the solvent in vacuo and purify by silica gel chromatography (9:1 hexane/ethyl acetate) to give (4-(carboxy)-4-(4-methoxybenzylthio)-1-(carbo-t-butyloxy)-piperidine as a white solid (0.5 g, 18%).

Mix (4-(carboxy)-4-(4-methoxybenzylthio)-1-(carbo-t-butyloxy)-piperidine (0.4 g, 1.04 8 mmol), EDC (0.302 g, 1.57 mmol) and tetrahydrofuran (10 mL). Treat with [4S-[4α, 7α(R*), 12bβ]]-7-(amino)-1,2,3,4,6,7,8,12b-octahydro-6-oxopyrido[2,1-a][2]benzazepine (0.242 g, 1.048 mmol) and stir at room temperature for 24 hours. Evaporate the solvent in vacuo, take the residue up in ethyl acetate (60 mL), wash with 5% sulfuric acid, saturated sodium hydrogen carbonate and brine (30 mL). Dry (Na$_2$SO$_4$), evaporate the solvent in vacuo and purify by silica gel chromatography (3:2 hexane/ethyl acetate followed by 1:1 hexane/ethyl acetate) to give the title compound as a white solid (320 mg, 52%).

Scheme A, steps b and c: [4S-[4α, 7α(R*), 12bβ]]-7-[(4-Thio-4-oxopiperidine)methylamino]-1,2,3,4,6,7,8,12b-octahydro-6-oxopyrido[2,1-a][2]benzazepine, trifluoroacetate salt Mix [4S-[4α, 7α(R*), 12bβ]]-7-[(4-(4-Methoxybenzylthio)-4-oxo-1-(carbo-t-butyloxy)-piperidine)methylamino]-1,2,3,4,6,7,8,12b-octahydro-6-oxopyrido[2,1-a][2]benzazepine (320 mg, 0.54 mmol), anisole (0.58 mL, 5.34 mmol), mercuric acetate (214 mg, 0.67 mmol) and methylene chloride (10 mL). Cool in an ice bath and treat with trifluoroacetic acid (3.5 mL) After 3.5 hours, bubble in H$_2$S gas for 10 minutes, filter and evaporate the solvent in vacuo. Triturate the residue with hexane (2×), add methylene chloride and filter. Evaporate the solvent in vacuo, adding carbon tetrachloride to remove excess trifluoroacetic acid. Dissolve the residue in a minimum amount of methylene chloride and pour into vigorously stirring hexane. Collect the precipitate by vacuum filtration and purify by silica gel chromatography (9:1:0.1 methylene chloride/methanol/ammonium hydroxide) to give [4S-[4α, 7α(R*), 12bβ]]-7-[(4-thio-4-oxo-1-(carbo-t-butyloxy)-piperidine)methylamino]-1,2,3,4,6,7,8,12b-octahydro-6-oxopyrido[2,1-a][2]benzazepine. Dissolve in methylene chloride (5 mL) and add trifluoroacetic acid (0.05 mL, 0.669 mmol) to give the title compound after filtration (0.141 mg, 54%).

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also potentiate endogenous levels of bradykinin.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) will generally vary from about 0.01 milligram per kilogram of body weight per day (mg/kg/day) to about 20 mg/kg/day. A daily dose of from about 0.1 mg/kg to about 10 mg/kg is preferred.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0.001% to about 75% of the composition by weight. Inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application. The compounds of Formula (I) wherein $B_1$ is hydrogen or alkoxy are preferred. Compounds of Formula (I) wherein Q is

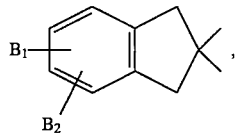

n is an integer 0 and
$R_1$ is hydrogen or acetyl are preferred.

The following specific compounds of Formula (I) are particularly preferred in the end-use application of the compounds of the present invention:

[4S-[4α, 7α(R*), 12bβ]]-7-[(2-Thio-2-oxoindan)methylamino]-1,2,3,4,6,7,8,12b-octahydro-6-oxopyrido[2,1-a][2]benzazepine;

[4S-[4α, 7α(R*), 12bβ]]-7-[(2-Acetylthio-2-oxoindan)methylamino]-1,2,3,4,6,7,8,12b-octahydro-6-oxopyrido[2,1-a][2]benzazepine; and

[4S-[4α, 7α(R*), 12bβ]]-7-[(4-Thio-4-oxopiperidine)methylamino]-1,2,3,4,6,7,8,12b-octahydro-6-oxopyrido[2,1-a][2]benzazepine.

What is claimed is:

1. A method of inhibiting enkephalinase in a patient in need thereof comprising administering to said patient an effective enkephalinase inhibitory amount of a compound of the formula

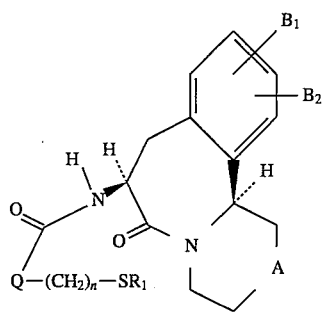

wherein $B_1$ and $B_2$ are each independently hydrogen; hydroxy; —$OR_2$ wherein $R_2$ is a $C_1$–$C_4$ alkyl or an Ar—Y group wherein Ar is aryl and Y is a hydrogen or $C_1$–$C_4$ alkyl; or, where $B_1$ and $B_2$ are attached to adjacent carbon atoms, $B_1$ and $B_2$ can be taken together with said adjacent carbons to form a benzene ring or methylenedioxy;

A is a bond, methylene, oxygen, sulfur, $NR_4$ or $NCOR_5$ wherein $R_4$ is hydrogen, a $C_1$–$C_4$ alkyl or an Ar—Y— group and $R_5$ is —$CF_3$ or a $C_1$–$C_{10}$ alkyl or an Ar—Y— group;

$R_1$ is hydrogen, acetyl, —$CH_2OC(O)C(CH_3)_3$ or benzoyl;

n is an integer 0 to 3; and

Q is a group of the formula

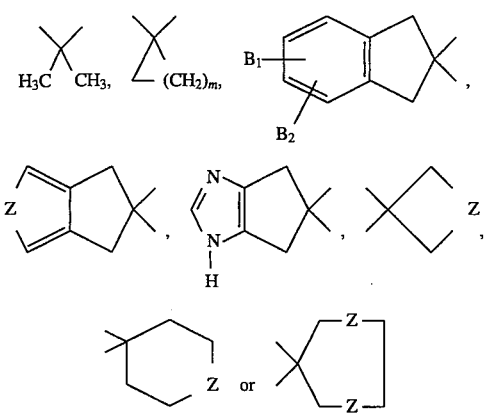

wherein Z is O, $NR_4$ or S; and m is an integer 1 to 5.

2. A method according to claim 1 wherein the patient is in need of an endorphin- or enkephalin-mediated analgesic effect.

3. A method according to claim 1 wherein the patient is in need of an ANP-mediated hypotensive effect.

4. A method according to claim 1 wherein the patient is in need of an ANP-mediated diuretic effect.

5. A method according to claim 1 wherein the patient is suffering from congestive heart failure.

* * * * *

UNITED STATES PATENT AND TRADEMARK OFFICE
CERTIFICATE OF CORRECTION

PATENT NO. : 5,491,141

DATED : February 13, 1996

INVENTOR(s) : Alan M. Warshawsky & Gary A. Flynn

It is certified that error appears in the above-identified patent and that said Letters Patent is hereby corrected as shown below:

Cover Page, Abstract, last line, patent reads: " Enkephalise " and should read -- Enkephalinase -- .
Column 1, Line 10, patent reads: " This is division " and should read -- This is a division -- .
Column 3, Line 15, patent reads: " refer " and should read -- refers -- .

Column 11, Line 41, patent reads: " 0.1 00 " and should read -- 0.100 -- .
Column 14, Line 12, patent reads: " [(2-92- " and should read -- [(2-(2- -- .
Column 14, Line 62, patent reads: " (i.90 " and should read -- (1.90 -- .

Column 24, Line 55, patent reads: " (8.82 g, 25 98%) " and should read -- (8.82g, 98%) --.
Column 29, Line 65, patent reads: " wit h " and should read -- with -- .
Column 30, Line 24, patent reads: " [2-a] " and should read -- [2, 1-a] -- .
Column 31, Line 11, patent reads: " for hour " and should read -- for 1 hour -- .
Column 32, Line 23, patent reads: " 1.04 8 " and should read -- 1.048 --.
Column 7, line 15, patent reads: "or $(R_4CO)_2$" and shoud read --or $(R_5CO)_2$--.

Column 16, line 27, patent reads: "12b8" and should read --12β--.

Column 21, line 20, patent reads: "$(Mg_2O_4)$" and should read --$(Mg_sO_4)$--."

Signed and Sealed this

Fifth Day of August, 1997

Attest:

BRUCE LEHMAN

*Attesting Officer*     Commissioner of Patents and Trademarks